(12) United States Patent
Mohindra et al.

(10) Patent No.: US 9,621,974 B2
(45) Date of Patent: Apr. 11, 2017

(54) DUAL PURPOSE PILL REMINDER AND TAMPER DETECTOR

(71) Applicants: Rajkumari Mohindra, Milpitas, CA (US); Rishi Mohindra, Milpitas, CA (US)

(72) Inventors: Rajkumari Mohindra, Milpitas, CA (US); Rishi Mohindra, Milpitas, CA (US)

(73) Assignee: Rajkumari Mohindra, Milpitas, CA (US)

( * ) Notice: Subject to any disclaimer, the term of this patent is extended or adjusted under 35 U.S.C. 154(b) by 723 days.

(21) Appl. No.: 13/897,444

(22) Filed: May 20, 2013

(65) Prior Publication Data
US 2014/0341411 A1    Nov. 20, 2014

(51) Int. Cl.
 G08B 3/10        (2006.01)
 G08B 21/24       (2006.01)
 (Continued)

(52) U.S. Cl.
 CPC ............... H04R 1/021 (2013.01); A61J 1/03 (2013.01); A61J 1/065 (2013.01); A61J 1/1418 (2015.05); A61J 7/0409 (2013.01); A61J 7/0436 (2015.05); B65D 51/248 (2013.01); B65D 55/028 (2013.01); H03K 17/955 (2013.01); A61J 7/0418 (2015.05); A61J 7/0481 (2013.01); A61J 2200/30 (2013.01); A61J 2200/76 (2013.01); A61J 2205/60 (2013.01); A61J 2205/70 (2013.01); B65D 2203/12 (2013.01); G06F 19/3462 (2013.01); G08B 13/149 (2013.01); G08B 13/1672 (2013.01);
(Continued)

(58) Field of Classification Search
 CPC .... H03K 17/955; G01R 27/2605; G01D 5/24; A61J 1/1412; A61J 1/1418; A61J 1/03
 See application file for complete search history.

(56) References Cited

U.S. PATENT DOCUMENTS 6,317,390 B1 *  11/2001  Cardoza ............... A61J 7/0481
                                                221/2
7,554,434 B1 *  6/2009  Gifford ................ A61J 7/0409
                                                215/230
(Continued)

Primary Examiner — Matthew F Desanto

(57) ABSTRACT

An audio signal analysis method is provided for detecting the opening and closing of a medicine bottle cap in a robust manner using a micro speaker and a microphone along with associated mixed signal electronics. It is also used for robust tamper detection and for monitoring liquid medication consumption accurately. In a preferred embodiment an unmodulated OFDM signal is used that covers the entire operating audio spectrum. In another embodiment, Complimentary code based phase encoding of the subcarrier phases is used to reduce the peak to average power of the OFDM signal, thereby enabling higher transmit power of the audio signal to mitigate against interference. A suitable wireless device can be co-located with the mixed signal electronics for sending the bottle usage, medication reminder alarm, and tamper status to the medication compliance monitoring system or to the user's cell phone. In some embodiments of the patent, electrical capacitance sensing is used to determine if the bottle is opened or closed.

4 Claims, 28 Drawing Sheets

(51) Int. Cl.
  *H04R 1/02* (2006.01)
  *A61J 7/04* (2006.01)
  *A61J 1/03* (2006.01)
  *A61J 1/06* (2006.01)
  *B65D 51/24* (2006.01)
  *B65D 55/02* (2006.01)
  *H03K 17/955* (2006.01)
  *A61J 1/14* (2006.01)
  *G08B 13/14* (2006.01)
  *G08B 13/16* (2006.01)
  *G06F 19/00* (2011.01)
  *H04R 3/00* (2006.01)

(52) U.S. Cl.
  CPC ............... *G08B 21/24* (2013.01); *H04R 3/00* (2013.01); *H04R 2400/00* (2013.01); *H04R 2410/00* (2013.01)

(56) References Cited

U.S. PATENT DOCUMENTS

| | | | |
|---|---|---|---|
| 8,963,710 B2* | 2/2015 | Huang | A61J 1/03 340/309.16 |
| 2005/0011163 A1* | 1/2005 | Ehrensvard | G08B 13/126 53/410 |
| 2011/0148651 A1* | 6/2011 | Hendrickson | D06F 39/02 340/686.6 |

* cited by examiner

FIGURE 3

| Musical Term | Physics Term | Frequency | Wavelength | | |
|---|---|---|---|---|---|
| | | | (a) | (b) | (c) |
| Fundamental | First Harmonic | f | 2L | 4L | 2L |
| First overtone | Second Harmonic | 2f | L | 4/3 L | L |
| Second overtone | Third Harmonic | 3f | 2/3 L | 4/5 L | 2/3 L |
| Third Overtone | Fourth Harmonic | 4f | 1/2 L | 6/7 L | 1/2 L |

DUAL PURPOSE PILL REMINDER AND TAMPER DETECTOR

RELATED APPLICATIONS

This application claims the benefit of U.S. Patent Provisional Application No. 61/653,890, filed May 31, 2012, and titled "DUAL PURPOSE PILL REMINDER AND TAMPER DETECTOR," which is herein incorporated by reference in its entirety.

The present application is related to U.S. Pat. No. 7,081,807 B2, issued Jul. 25, 2006, for AUTOMATIC PILL REMINDER BOTTLES, included by reference herein.

The present application is related to U.S. Pat. No. 6,604,650 B2, issued Aug. 12, 2003, for BOTTLE-CAP MEDICATION REMINDER AND OVERDOSE SAFEGUARD, included by reference herein.

The present application is related to United States patent number US 2007/0016443 A1, issued Jan. 18, 2007, included by reference herein.

The present application is related to U.S. Pat. No. 4,424,911, issued Jan. 10, 1984, for CONTAINER TAMPER DETECTION DEVICE, included by reference herein.

The present application is related to U.S. Pat. No. 5,862,182, issued Jan. 19, 1999, for OFDM DIGITAL COMMUNICATIONS SYSTEMS USING COMPLIMENTARY CODES, included by reference herein.

The present application is related to United States patent number US 2008/016 2996 A1, issued Jul. 3, 2008, for MULTI-TOUCH AUTO SCANNING, included by reference herein.

FIELD OF THE INVENTION

The present invention relates to medicine bottle to help the users remember to take their pills or liquid medication. It also relates to tamper detection of bottles. More specifically it relates to methods for detecting the opening and closing of pill bottles in a robust tamper-proof manner.

BACKGROUND OF THE INVENTION

Millions of conventional bottles contain non-food, food, food supplements or medications sold to consumers every day. For most medical or health related applications, the contents (pills inside these bottles) have to be taken regularly. Keeping track of regular doses of medications can be difficult. Skipping or over dosages of certain medications can be deadly. Unfortunately, these millions of sold (pill) bottles have no intelligence to notify or remind their owners to take the contents inside the bottles. Some other reminder devices do exist, but they are expensive to build, complicated to use, take extra shelve/drawer storage space to store and, most of all, those reminder devices are not compatible and cannot convert conventional bottles and conventional bottle caps into reminder bottles. There are needs for a user-friendly, simple, low-cost, effective and better way to "convert" these conventional dumb bottle or their caps into smart reminder device to remind users to take the contents inside these bottles.

Medication non-compliance is a major problem in healthcare. Physicians prescribe medications for a large class of chronic, asymptomatic diseases. These medications must typically be taken daily for the rest of the patient's life in order to sustain quality of life and reduce health risks.

Many food and drug substances are distributed within bottle containers. Because these substances are destined for human consumption, there is desired that the container never be opened prior to use by the ultimate owner and user of the bottle. Unfortunately, present bottles can be opened, and foreign or even poison sub-stances added, without a clear indication later that the bottle has been opened. Consequently it is desired to provide a device which will signal that a container has been opened.

Various prior art exist today for detecting the opening and closing of pills bottles using mechanical switches or infrared transceivers coupled to bottle caps, and for conveying that information electronically to a patient monitoring and compliance system, and for reminding patients regarding the dosage. Prior art exists for tamper detection of bottles and containers using mechanically coupled switches, with tamper related information conveyed to point of sales terminal or monitoring system using RFID or other wireless based solutions. No solution is known for monitoring and reminding dosage for liquid medication, or for their tamper detection, other than visible seals that could potentially be carefully broken and put back.

Mechanical switches in bottle caps can get contaminated and may be difficult to clean. They can get jammed or could fail. They are not good for liquid medication. They are not good for tamper detection as the switch could be fooled by mechanical means. Infrared transmitter and detector surface can get covered with contamination, and could be fooled for tamper detection. There are no known solutions that can combine tamper detection with dosage monitoring in an economical way suitable for mass markets.

It would be advantageous to provide a robust non-mechanical means for detection of opening and closing of a medicine bottle so that the mechanism is free from contamination and mechanical failures, and that can work with liquid medication.

It would also be advantageous to provide an opening and closing detection of a medicine bottle that can be used for foolproof tamper detection.

It would further be advantageous to provide an opening and closing detection of a medicine bottle that can be integrated into a patient medication compliance monitoring network and system.

SUMMARY OF THE INVENTION

In accordance with the present invention, a method is provided for detecting the opening and closing of a bottle cap in a robust manner. An audio micro speaker is used to generate standing waves inside the bottle enclosure. An audio microphone is used to measure the corresponding sound intensity inside the enclosure. Through spectral analysis of the audio signal using electronic means, the open and closed conditions of the bottle are determined in a robust way, and this determination is also used for detection of tampering of the bottle.

Audio spectral analysis is also used to determine the length of the resonating chamber above the surface of liquid medication. This can be used to monitor the liquid medication consumption accurately in either a medicine bottle or in a liquid medication dispensing container.

Both the audio microphone and speaker can be housed in the bottle cap or on top of it or at the base of the bottle or adjacent to the side of the bottle, along with suitable electronics for generating and analyzing sound signal and for performing various other tasks that may include monitoring of opening and closing of said cap, keeping track of timing of said opening and closing of cap, displaying various information for example like battery charge level or time elapsed since last usage of medicine, providing visual alarm or status, sounding reminder or tamper alarm, programming of usage and timing parameters, communicating with an electronic data network for conveying usage or tampering related information, sending reminder messages, and receiving usage programming parameters.

The standing wave produced by the micro speaker could be based on swept tone to cover the audio frequency band of interest, or in a preferred embodiment it could be based on an un-modulated Orthogonal Frequency Division Multiplexed (OFDM) signal that covers the entire spectrum of said frequency band of interest simultaneously with equally spaced frequency tones called subcarriers. In another embodiment, Complimentary code based phase encoding of each subcarrier phase is done in order to reduce the peak to average power of the OFDM signal, thereby enabling higher transmit power of the audio signal to mitigate against very loud external noise or vibration of the bottle when it is placed in a moving vehicle or in an airplane especially with rattling pills inside the bottle.

A suitable wireless device can be co-located with the above electronics for sending the bottle opening and closing timestamps, medication reminder alarm, and tamper status to the medication compliance monitoring system or to the user's cell phone. The wireless device could be based on Low Power Bluetooth, Bluetooth, RFID, Zigbee, IEEE802.15.4g, Wireless Local Area Network (WLAN) or it could be a transmit only device that is continuously monitored by a base station nearby. The base station could monitor multiple bottles for multiple users and act as a bridge to the Internet or to the user's data network.

The bottle or its cap can have an audiovisual indication about dosage reminder, and it could have an alphanumeric display that could show the amount of time elapsed since the last medication was taken. It can have buttons to enter dosage times and other user data.

The electronics comprises of an embedded microcontroller with optional digital signal processor and hardware accelerators e.g. for Fast Fourier Transform (FFT), memory (including but not limited to RAM, ROM, OTP, Flash, EPROM), A/D, D/A, timers and counters, quartz-based or non-quartz-based clocks, display driver, USB port, serial communication port, parallel communication port, other digital or analog or mixed signal blocks, and rechargeable or non-rechargeable battery.

Some embodiments of the patent uses capacitive sensing to determine if the bottle is opened or closed.

BRIEF DESCRIPTION OF THE DRAWINGS

A complete understanding of the present invention may be obtained by reference to the accompanying drawings, when considered in conjunction with the subsequent, detailed description, in which:

FIG. 3 is a diagram showing the relationship between the resonance frequency and the wavelength in terms of the length L of the resonating chamber;

For purposes of clarity and brevity, like elements and components will bear the same designations and numbering throughout the Figures.

DESCRIPTION OF THE PREFERRED EMBODIMENT

Figure 1:
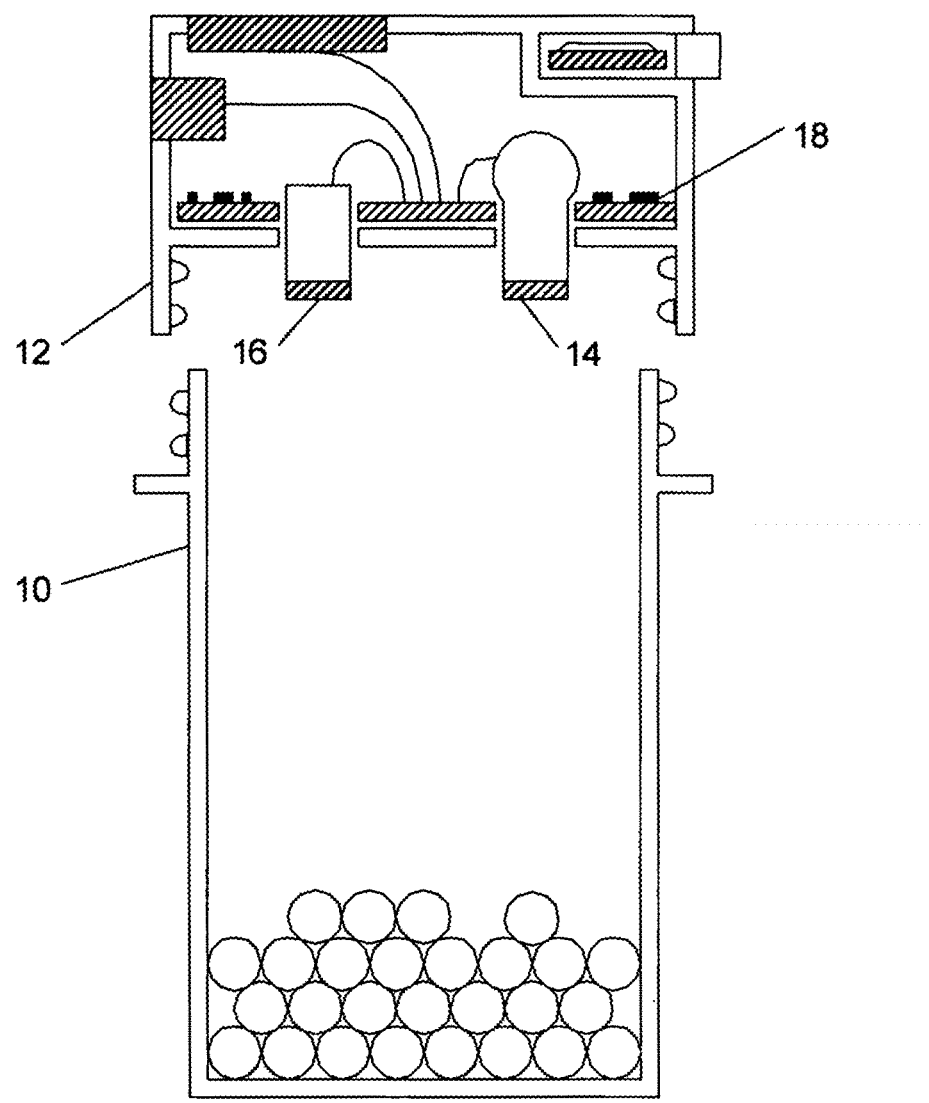
FIG. 1 is a cross-section of the bottle showing an exemplary placement of the microphone and speaker along with the associated electronics and some electrical connections in the bottle cap.

FIG. 1 is a cross-section of the Bottle 10 showing an exemplary placement of the microphone 16 and Speaker 14 along with the associated Electronics 18 in the Cap 12. Also shown are individual components being connected to a circuit board that holds an embedded microcontroller that is part of the electronics 18. Electronics 18 is depicted later in FIG. 4.

Figure 2:
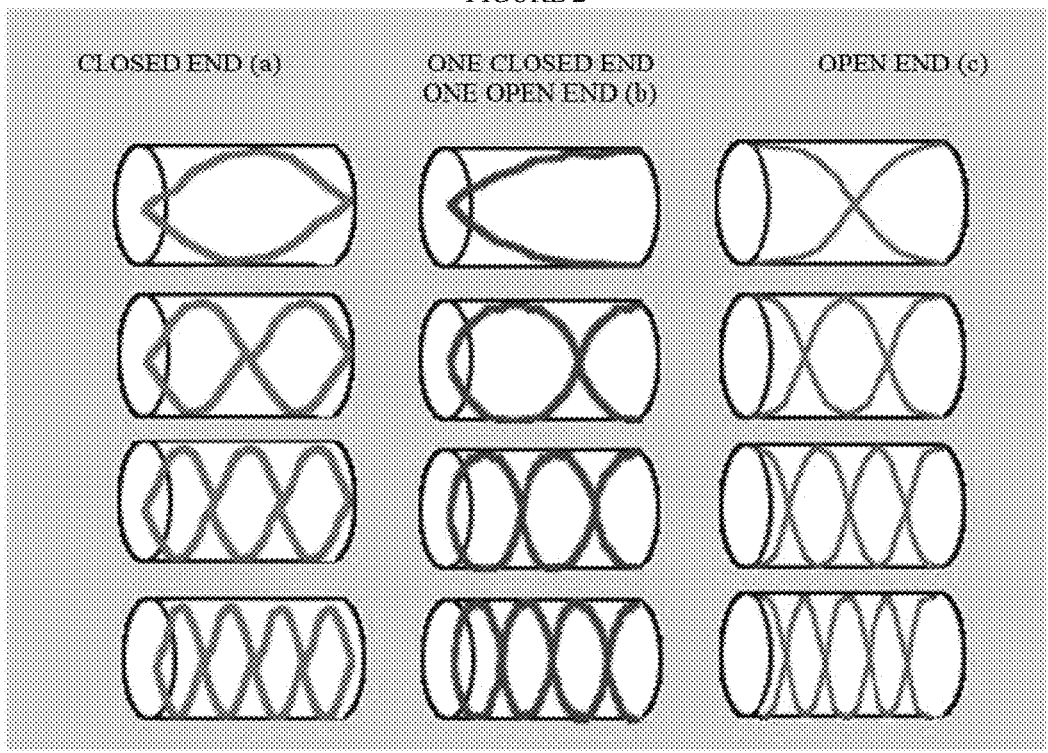
FIG. 2 is a diagram showing the location of the nodes and anti-nodes in a resonating chamber.

FIG. 2 shows the location of the nodes and anti-nodes in a resonating chamber of length L.

FIG. 3 shows the relationship between the resonance frequency and the wavelength in terms of the length L of the resonating chamber.

Figure 4:
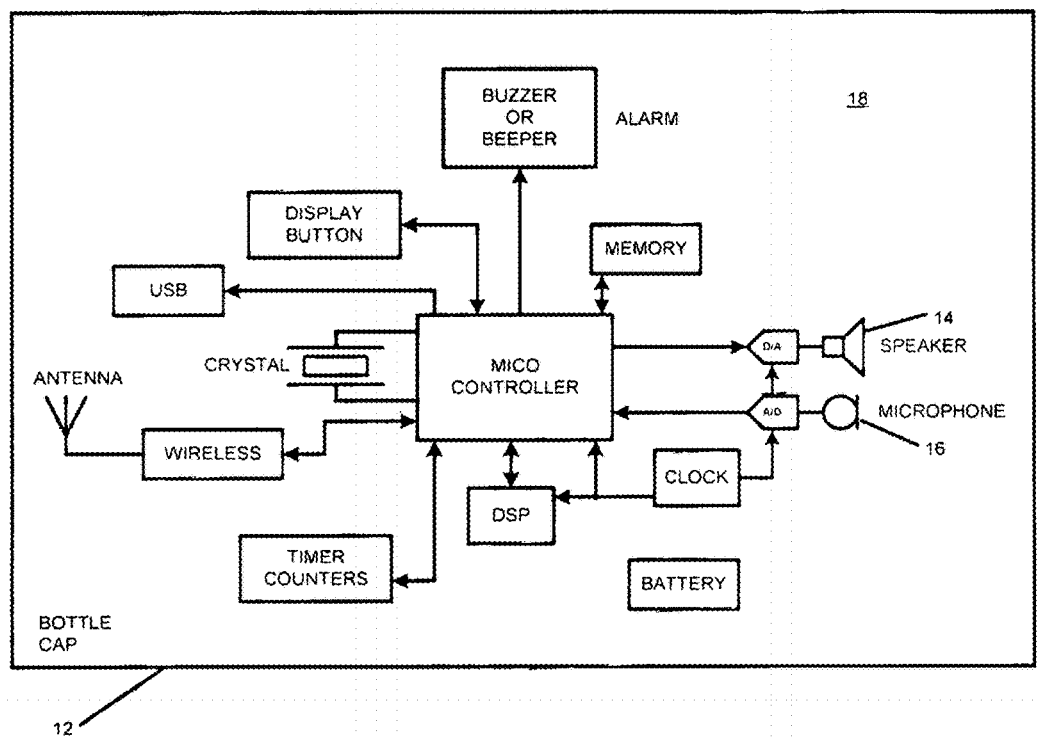
FIG. 4 is a diagram showing the blocks of the electronics inside the bottle cap. The electronics is used for generating and processing the acoustic signal in the bottle, and for providing the reminder alarm signal and tampering detection signal.

FIG. 4 shows the block diagrams of the Electronics 18 used for generating and processing the acoustic signal in the Bottle 10.

Figure 5:
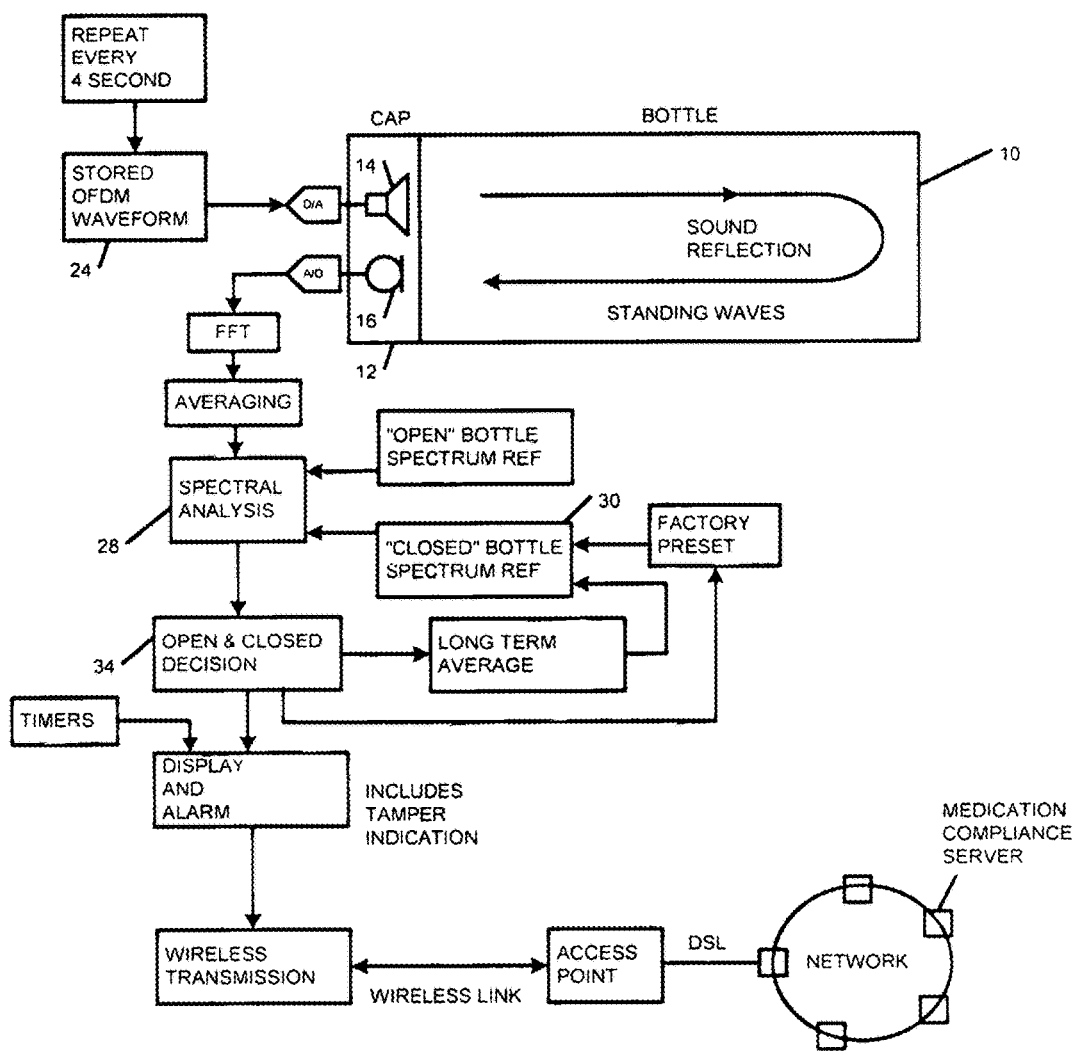
FIG. 5 is a diagram of the signal processing associated with the OFDM audio signal that is used for detecting the open and closed conditions of the bottle through channel sounding. Also shown is a wirelessly linked medication compliance monitoring and administration server network.

FIG. 5 shows a block diagram of the signal processing associated with the OFDM audio signal that is used for detecting the open and closed conditions of the Bottle 10. Also shown is a wirelessly linked medication compliance monitoring and administration server network.

Figure 6:
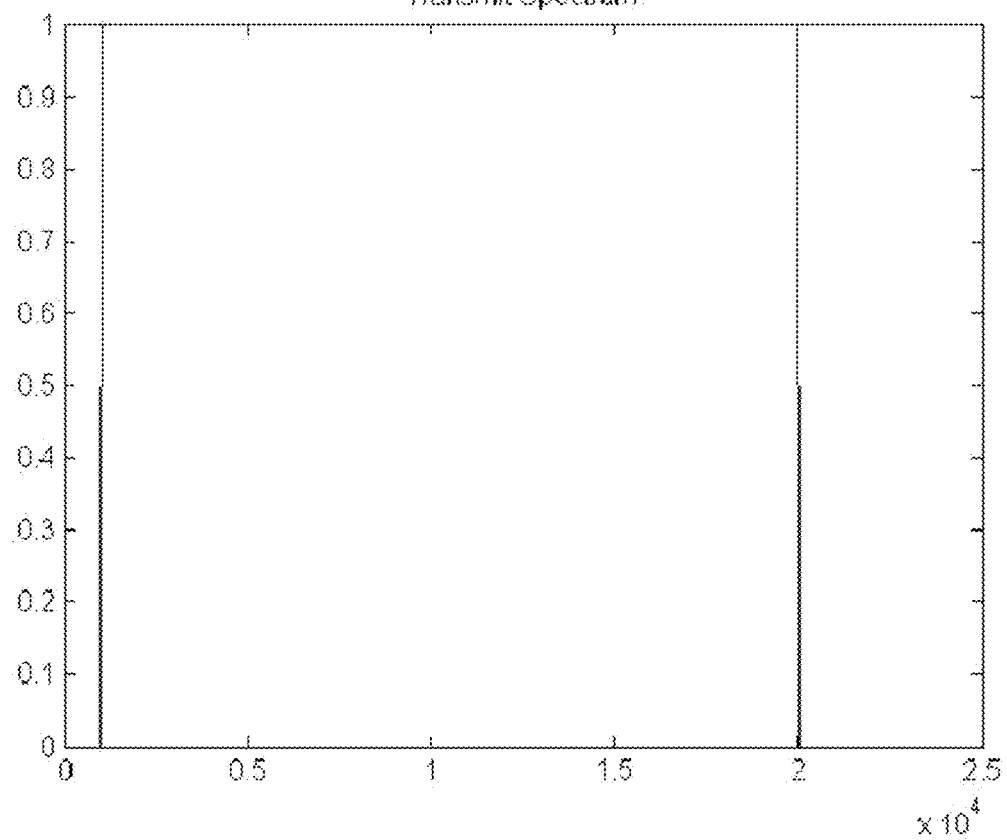
FIG. 6 is a transmitted un-modulated OFDM spectrum occupying the band from 200 Hz to 20 kHz. The signal spectrum shown is flat in this band, with a normalized level of 1, but it could be pre-emphasized to compensate for the combined frequency response of the speaker and microphone.

FIG. 6 is a transmitter un-modulated OFDM spectrum occupying the band from 200 Hz to 20 kHz. The signal spectrum shown is flat in this band, with a normalized level of 1, but it could be pre-emphasized to compensate for the combined frequency response of the speaker and microphone.

Figure 7:
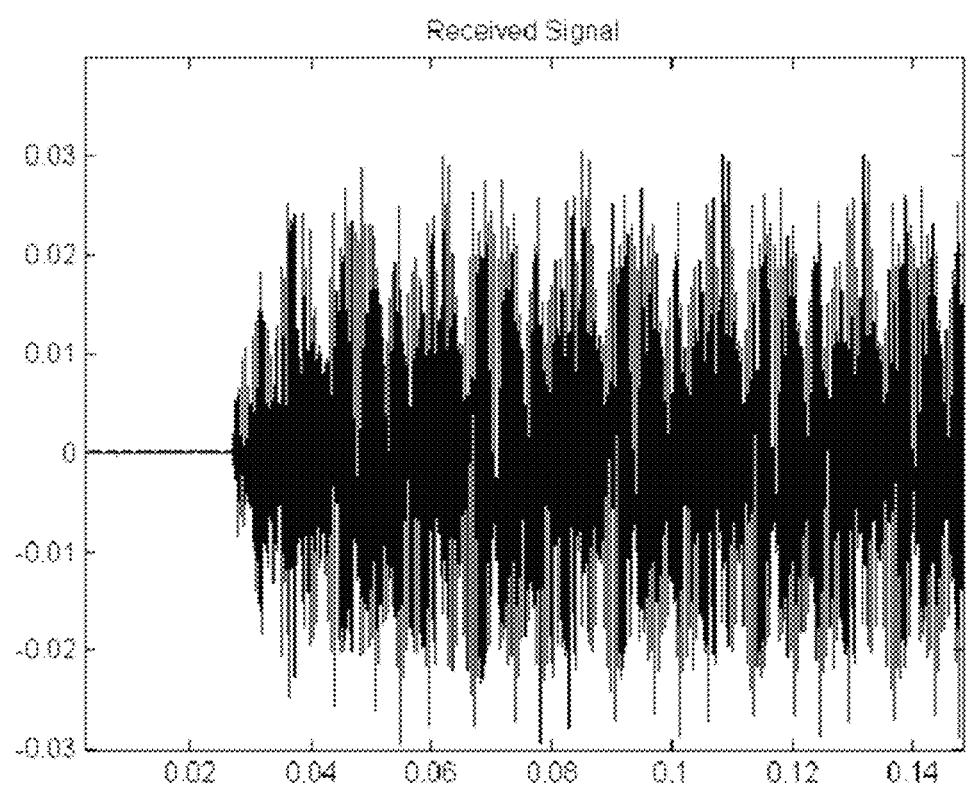
FIG. 7 is a received audio time domain signal. The currently used electronics system delay along with the resonance buildup is approximately 60 to 80 ms.

FIG. 7 shows the received audio time domain signal corresponding to the transmitted OFDM signal. The resonance takes approximately 60 to 80 ms to stabilize, and is based on a medicine Bottle 10 that is approximately 8.5 cm long.

Figure 8:
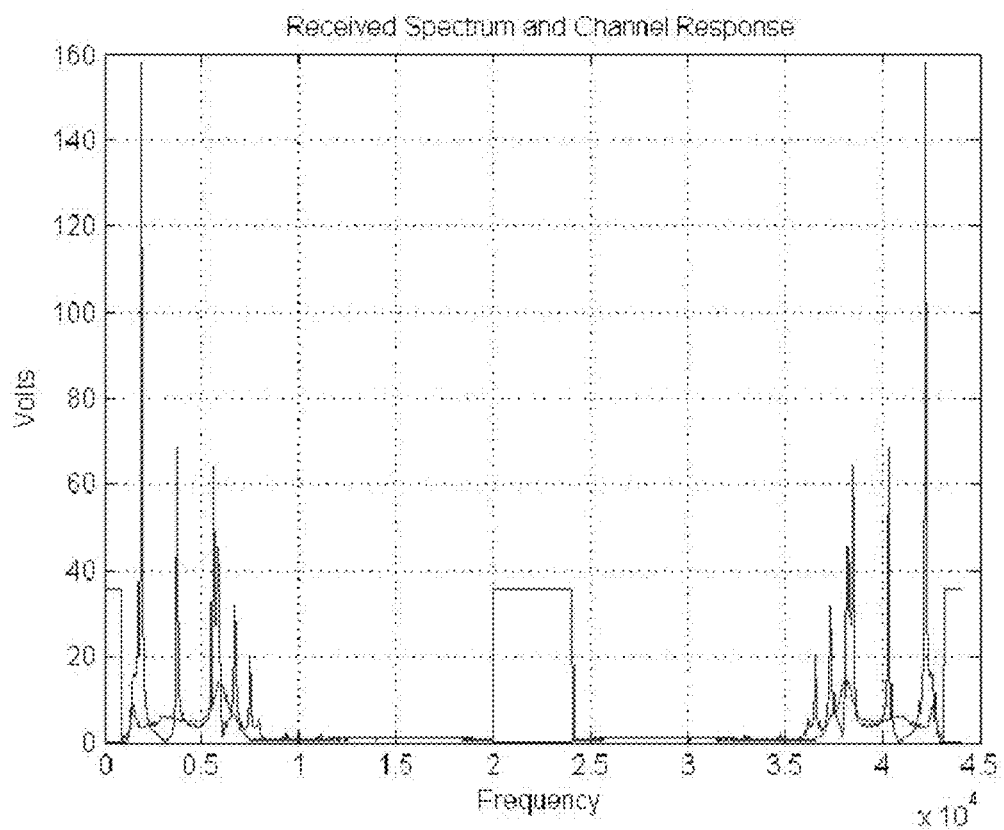
FIG. 8 is an overlapped received audio signal spectrum for the case when the bottle is open, and for the case when the bottle is closed. It is based on a medicine bottle that is approximately 8.5 cm long. There are strong resonances and anti-resonances up to 8 khz.

FIG. 8 shows the overlapped received audio signal spectrum for the case when the Bottle 10 is open, and for the case when the Bottle 10 is closed.

Figure 9:
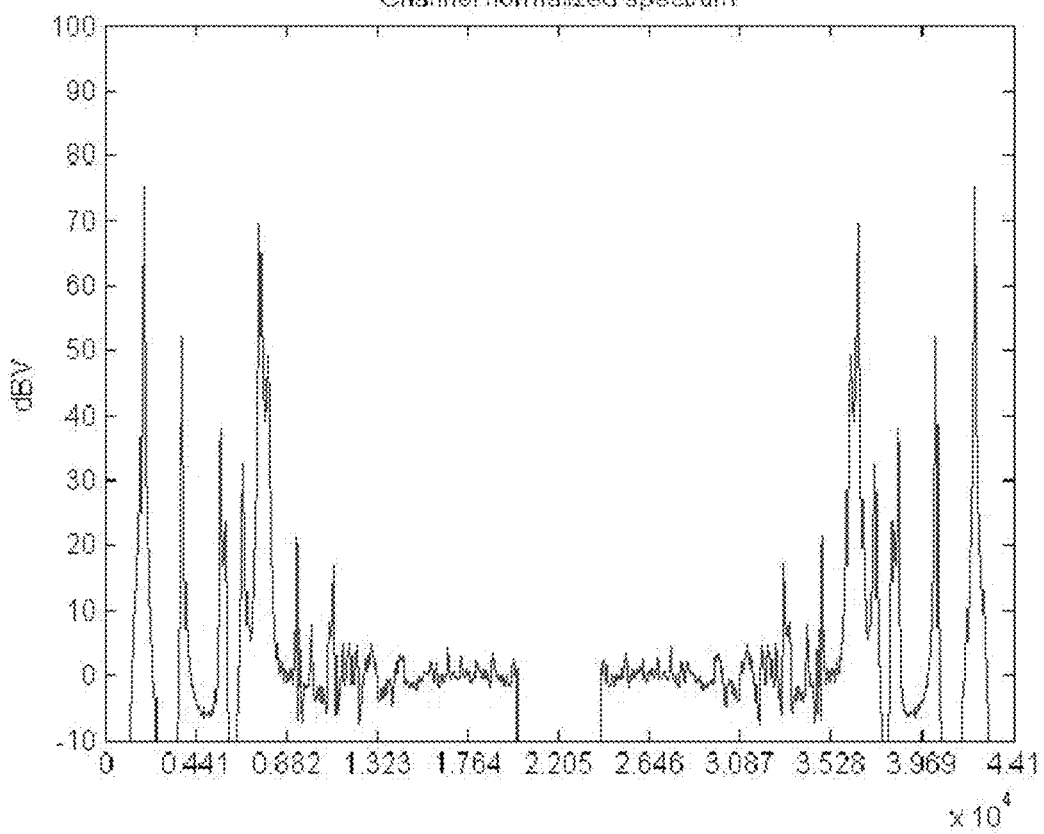
FIG. 9 is a normalized audio spectrum when the bottle is closed. It is normalized to the frequency response that corresponds to the case when the bottle is open.

FIG. 9 shows the normalized audio spectrum when the Bottle 10 is closed. It is normalized to the frequency response that corresponds to the case when the Bottle 10 is open.

Figure 10:
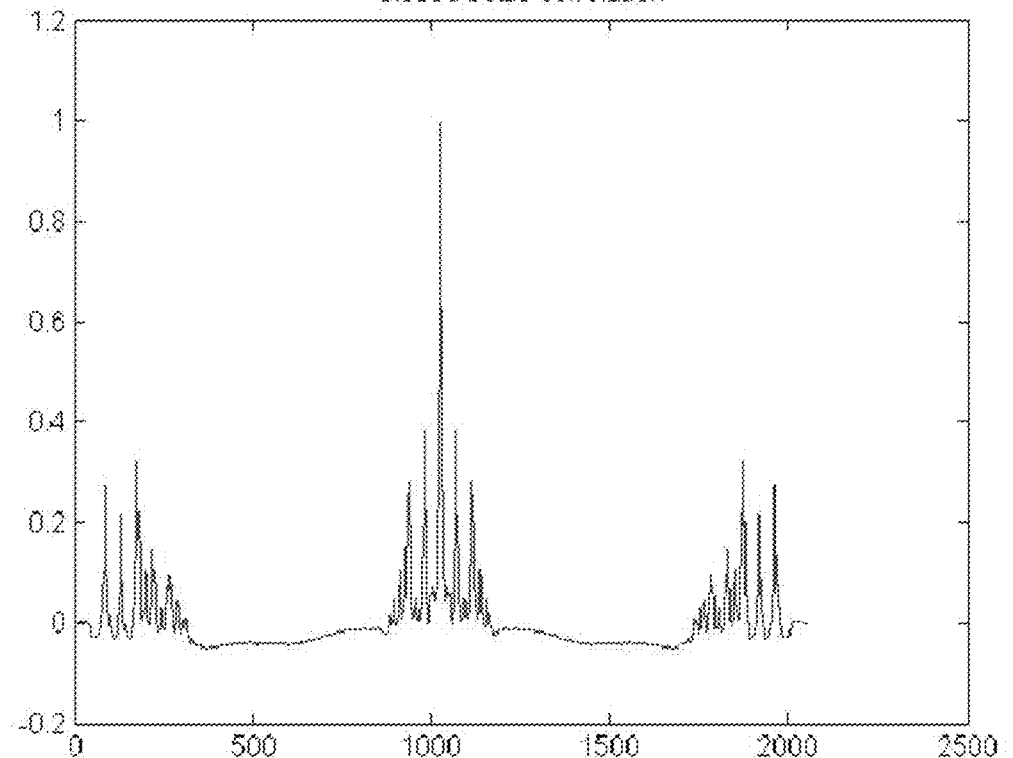
FIG. 10 is a cross-correlation of the closed bottle signal spectrum with an earlier stored spectrum corresponding to when the bottle was closed.

FIG. 10 is the cross-correlation of the closed bottle 10 signal spectrum with an earlier stored spectrum corresponding to when the bottle 10 was closed.

Figure 11:
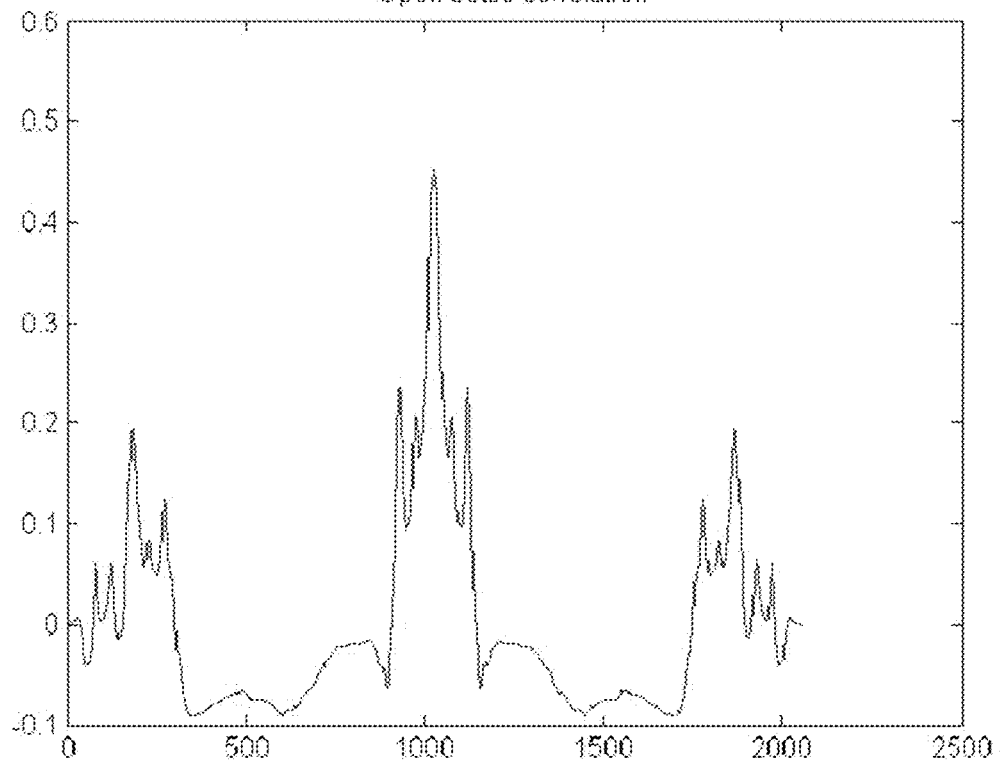
FIG. 11 is a cross-correlation between the spectrum of the closed bottle and the open bottle.

FIG. 11 is the cross-correlation between the spectrum of the closed bottle 10 and the open bottle 10.

Figure 12:
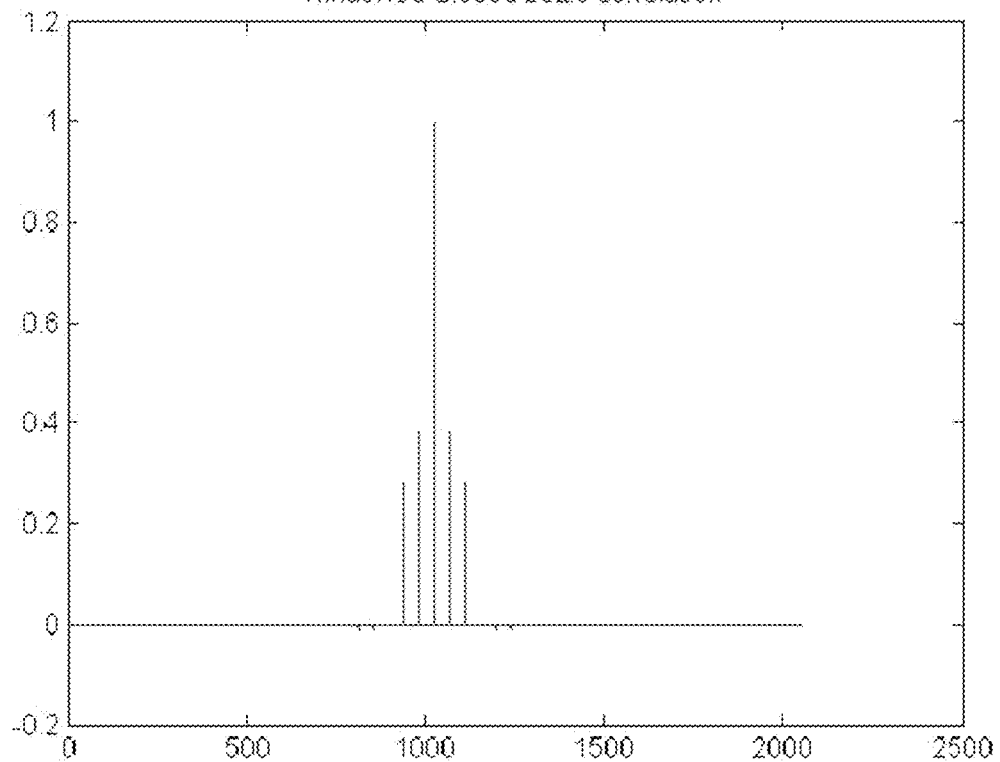
FIG. 12 is a windowed analyses of the cross-correlation of the spectrum when the bottle is closed to earlier stored spectrum corresponding to when the bottle was closed.
Figure 13:
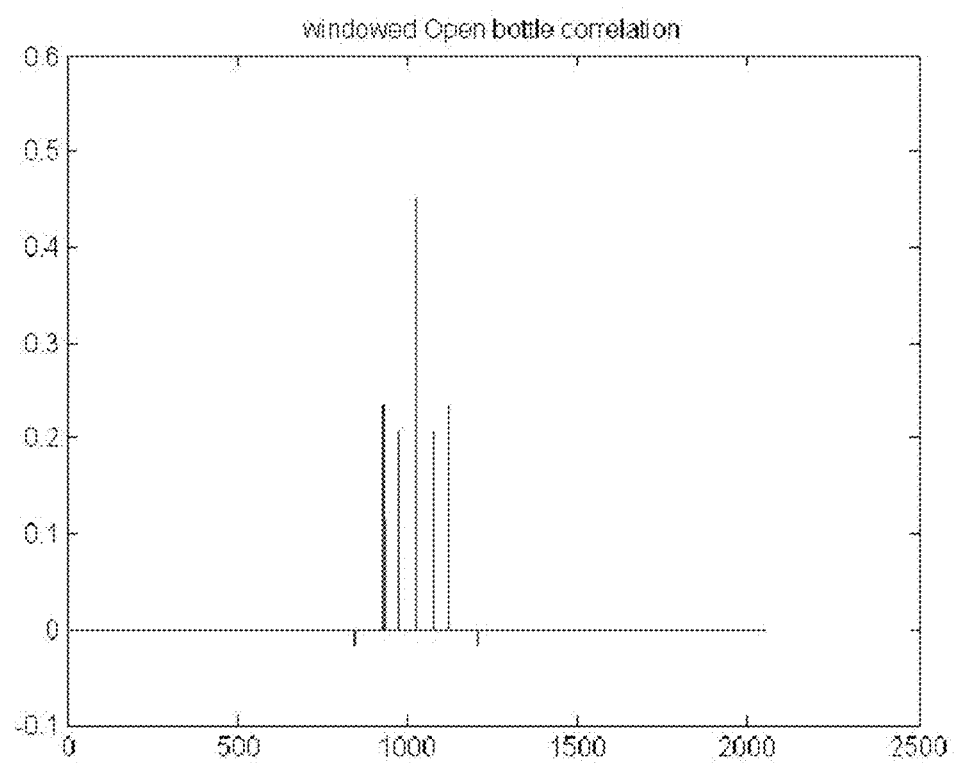
FIG. 13 is a windowed analysis of the cross-correlation of the spectrum when the bottle is open and when the bottle is closed.

FIG. 12 is a windowed analyses of the cross-correlation of the spectrum when the bottle 10 is closed to earlier stored spectrum corresponding to when the bottle 10 was closed FIG. 13 is a windowed analysis of the cross-correlation of the spectrum when the bottle 10 is open and when the bottle 10 is closed.

Figure 14:
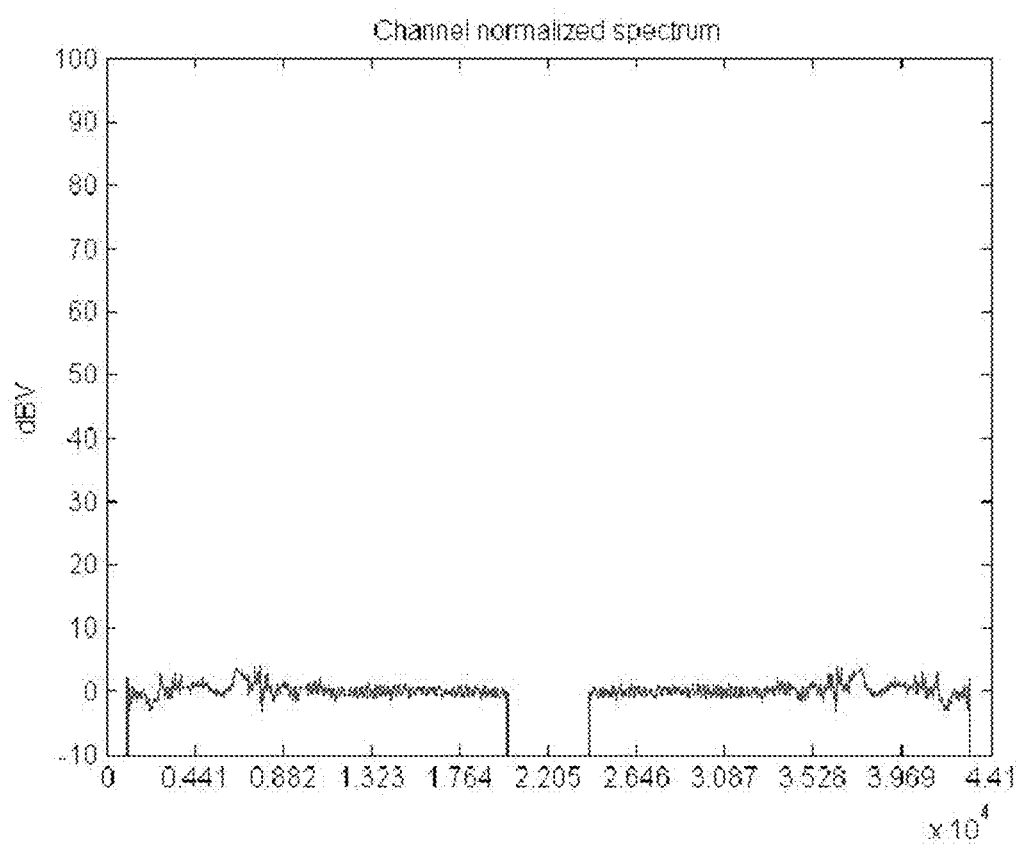
FIG. 14 is a normalized audio spectrum when the bottle is open.

FIG. 14 shows the normalized audio spectrum when the Bottle 10 is open.

Figure 15:
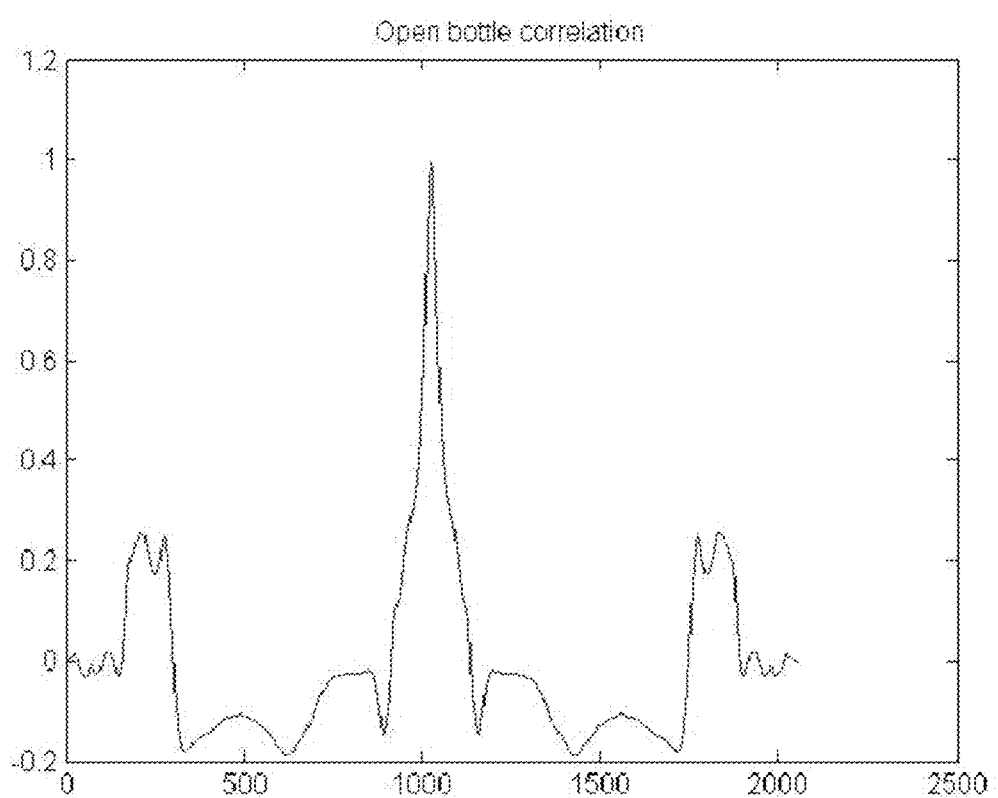
FIG. 15 is a cross-correlation of the spectrum with stored version, both corresponding to when the bottle is open.

FIG. 15 is cross-correlation of the spectrum with stored version, both corresponding to when the bottle 10 is open.

Figure 16:
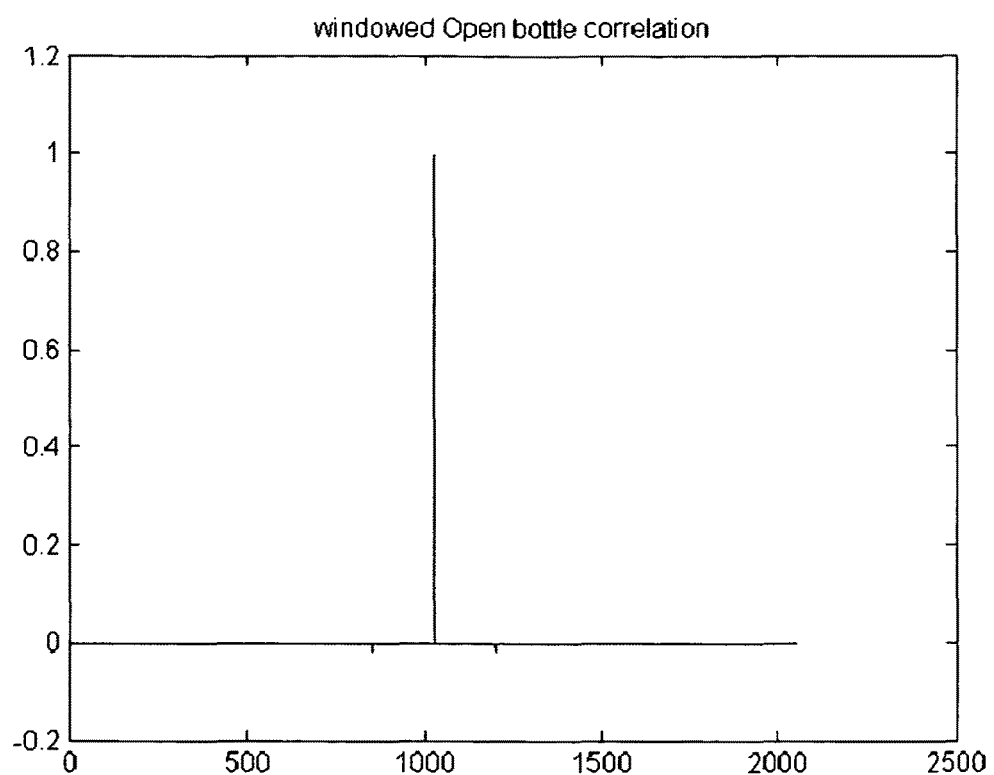
FIG. 16 is a windowed analysis of the cross-correlation of the signal spectrum when the bottle is open, with an earlier stored spectrum corresponding to the open bottle. Note that it is a delta function since both the broadband spectra are flat.
Figure 17:
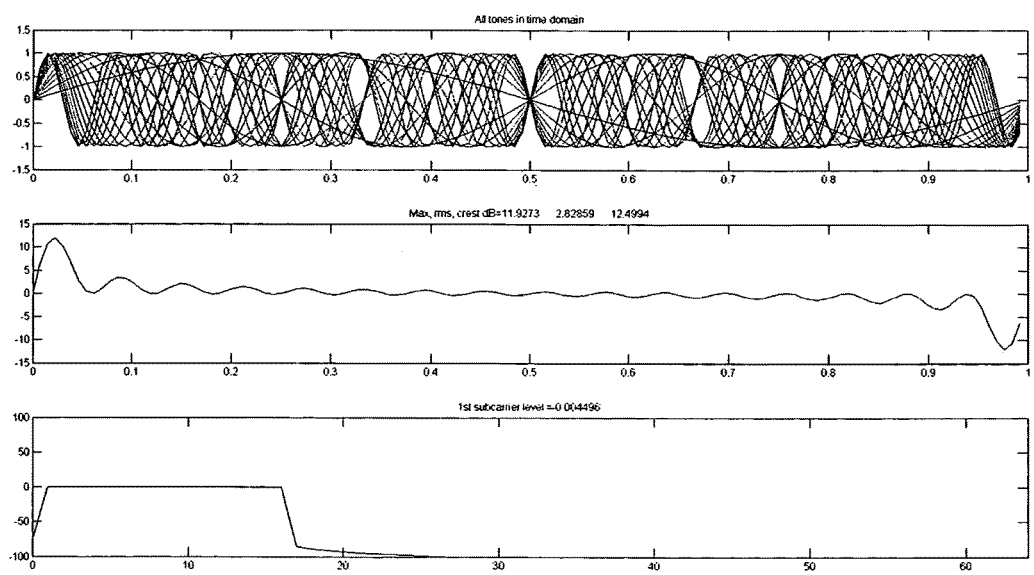
FIG. 17 is an un-modulated OFDM signal for 16 subcarriers without incorporating any peak to average power ratio (PAPR) reduction method. The top graph shows the time domain waveform of each subcarrier, the middle graph shows the composites time domain OFDM signal, and the bottom graph shows the spectrum of the OFDM signal.
Figure 18:
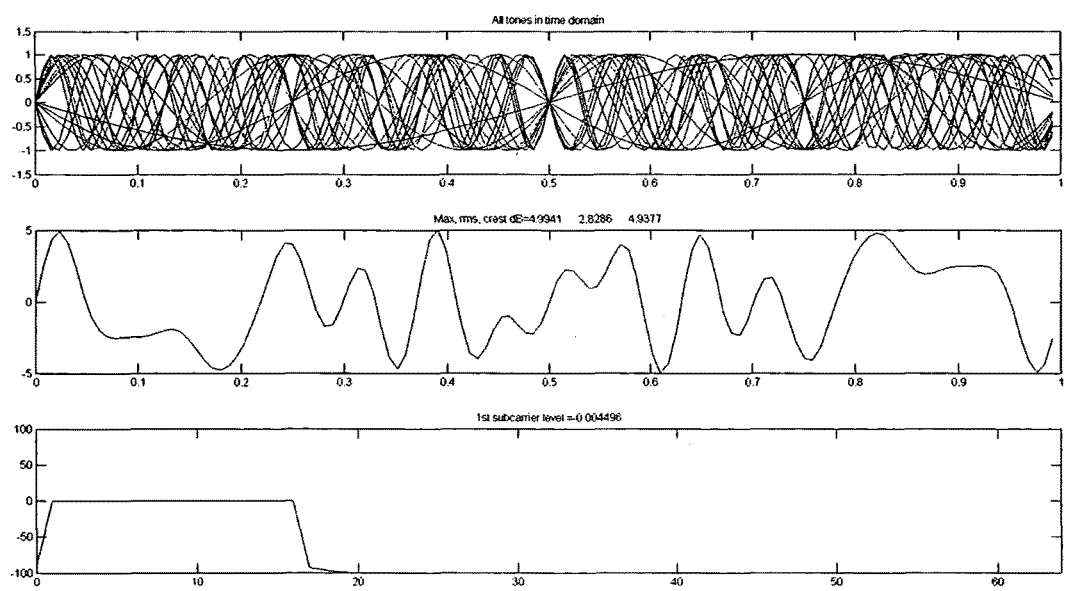
FIG. 18 is an un-modulated OFDM signal with 16 subcarriers, using complimentary code based PAPR reduction. The top graph shows the time domain waveform of each subcarrier, the middle graph shows the composites time domain OFDM signal, and the bottom graph shows the spectrum of the OFDM signal.
Figure 19:
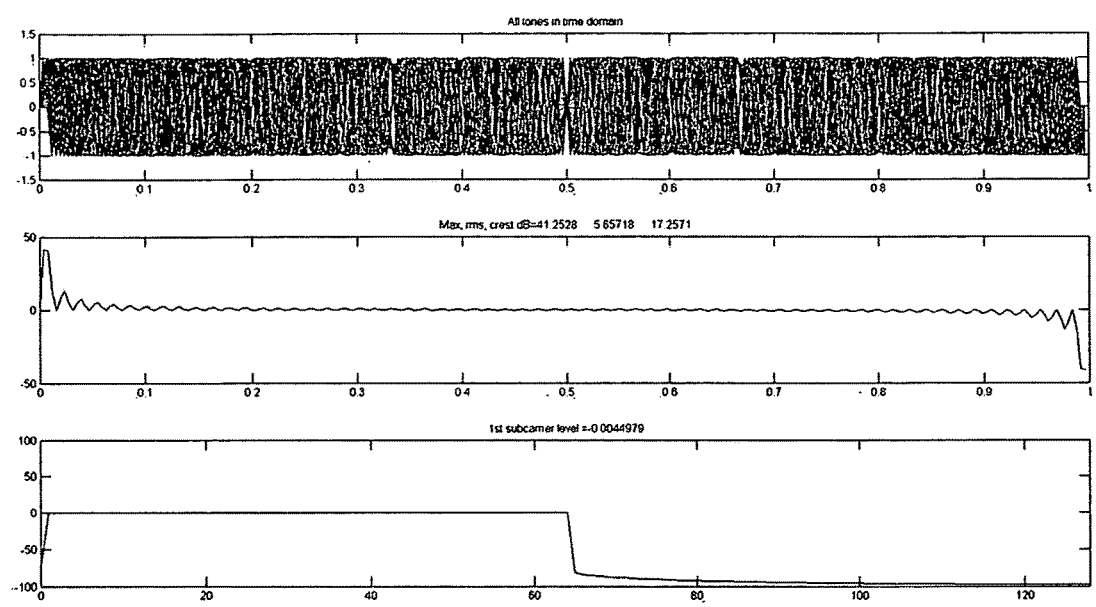
FIG. 19 is an un-modulated OFDM signal for 64 subcarriers without PAPR reduction. The top graph shows the time domain waveform of each subcarrier, the middle graph shows the composites time domain OFDM signal, and the bottom graph shows the spectrum of the OFDM signal.
Figure 20:
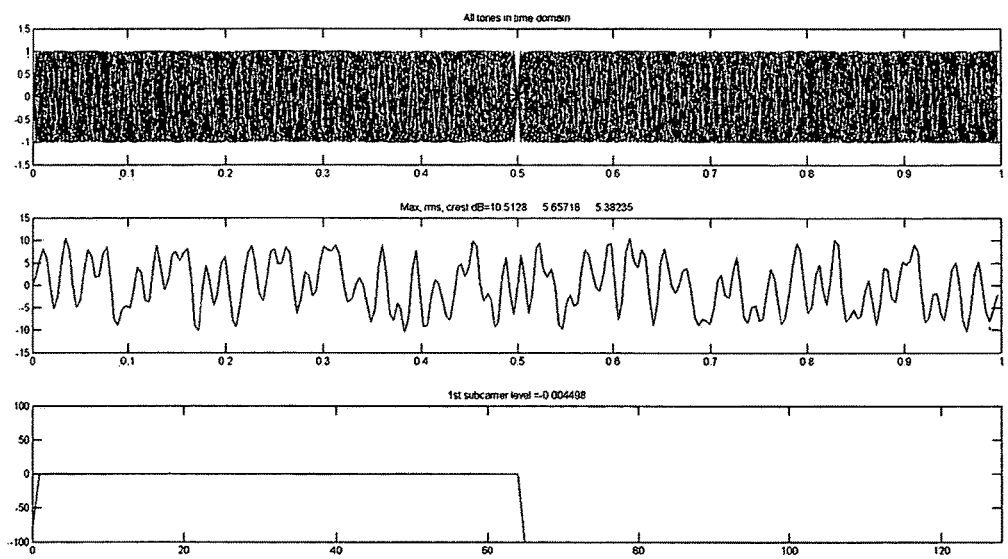
FIG. 20 is an un-modulated OFDM signal with 64 subcarriers, using complimentary code based peak to average power ratio (PAPR) reduction. The top graph shows the time domain waveform of each subcarrier, the middle graph shows the composites time domain OFDM signal, and the bottom graph shows the spectrum of the OFDM signal.

FIG. 16 is windowed analysis of the cross-correlation of the signal spectrum when the bottle 10 is open, with an earlier stored spectrum corresponding to the open bottle 10. Note that it is a delta function since both the broadband spectra are flat.

FIGS. 17 through 20 show the OFDM signals for 16 and 64 subcarriers. The top graphs show the subcarrier waveforms in the time domain. The middle graph shows the composites OFDM Signal 24 in the time domain. The lower graph shows the spectrum of the OFDM Signal 24 in the frequency domain.

Figure 21:
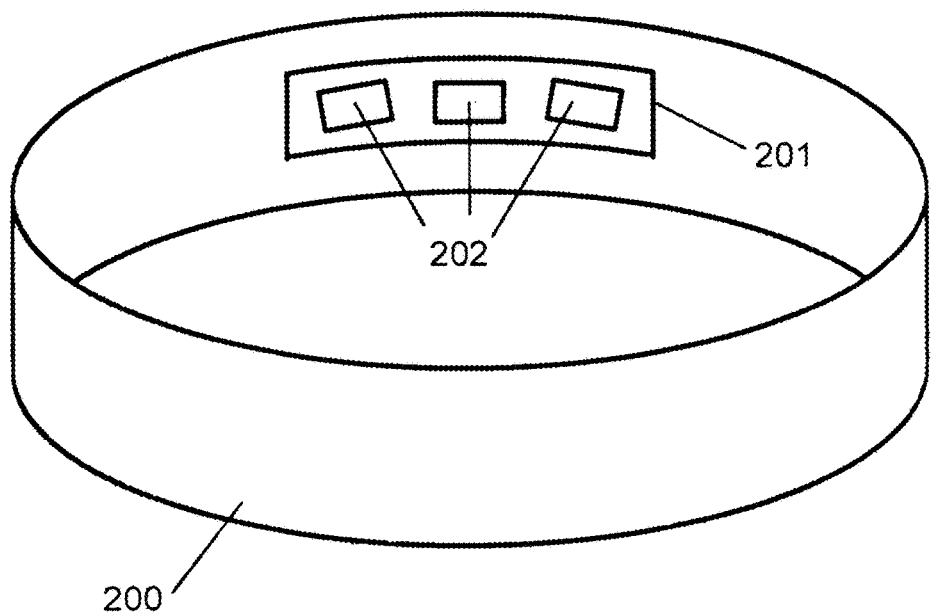
FIG. 21 is a diagram showing conductive electrodes integrated into the cap of a bottle.

FIG. 21 is a Diagram showing the conductive electrodes integrated into the cap 12 of a bottle 10.

Figure 22:
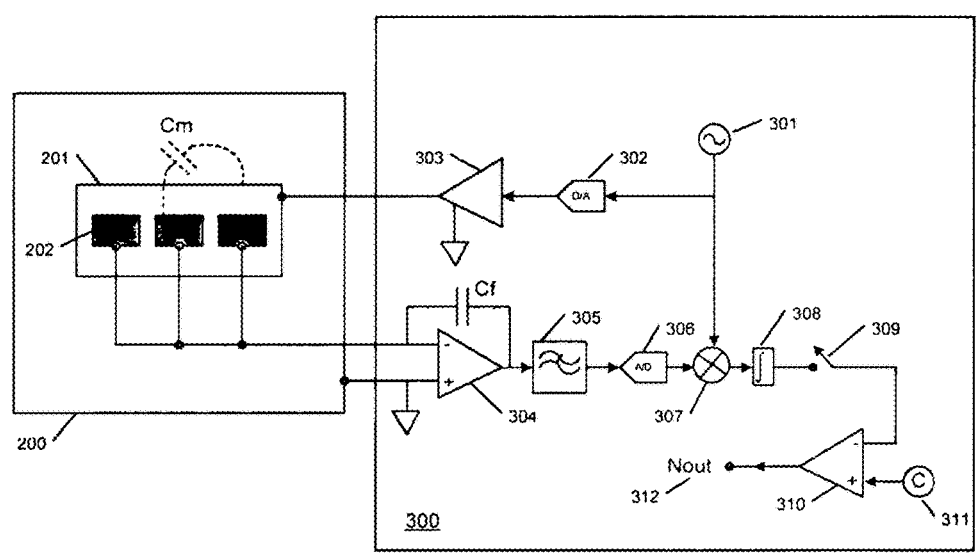
FIG. 22 is a block diagram of part of the electronics along with the electrodes in the cap.

FIG. 22 is a block diagram of part of the electronics 18 for capacitive sensing along with the electrodes in the cap 12.

Figure 23:
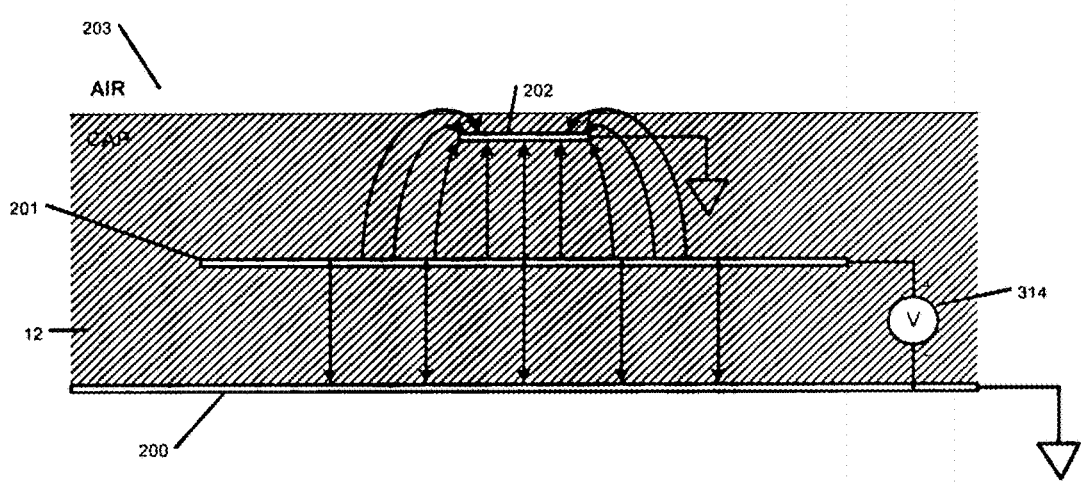
FIG. 23 is a cross-sectional view showing the dielectric stack up of the electrodes in the cap when it is not screwed onto the bottle.

FIG. 23 is a cross-sectional view showing the dielectric stack up of the electrodes in the cap 12 when it is not screwed onto the bottle 10.

Figure 24:
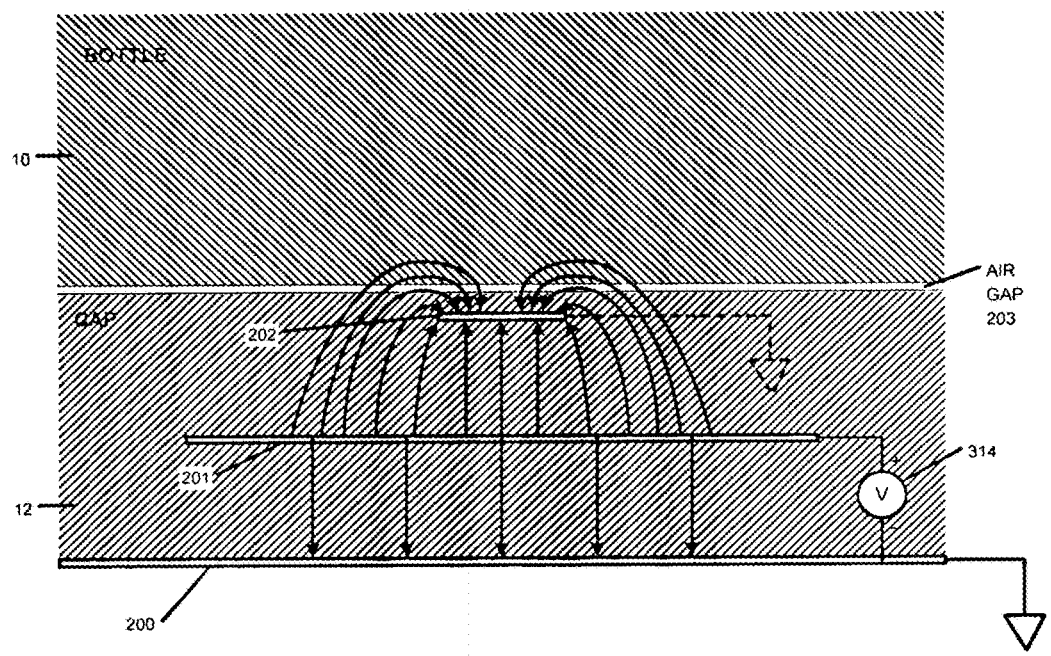
FIG. 24 is a cross-sectional view showing the dielectric stack up of the electrodes in the cap when it is screwed onto the bottle.

FIG. 24 is a cross-sectional view showing the dielectric stack up of the electrodes in the cap 12 when it is screwed onto the bottle 10.

Figure 25:
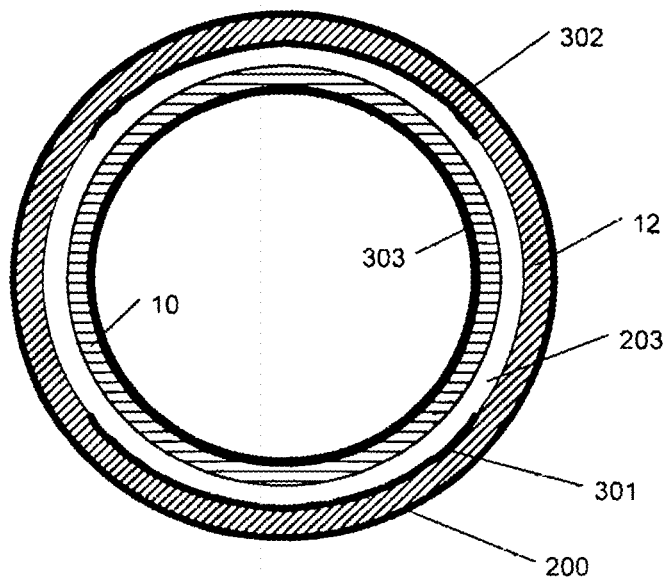
FIG. 25 is a top cross-sectional view of the cap when it is screwed onto the bottle.

FIG. 25 is a top cross-sectional view of the cap 12 when it is screwed onto the bottle 10.

Figure 26:
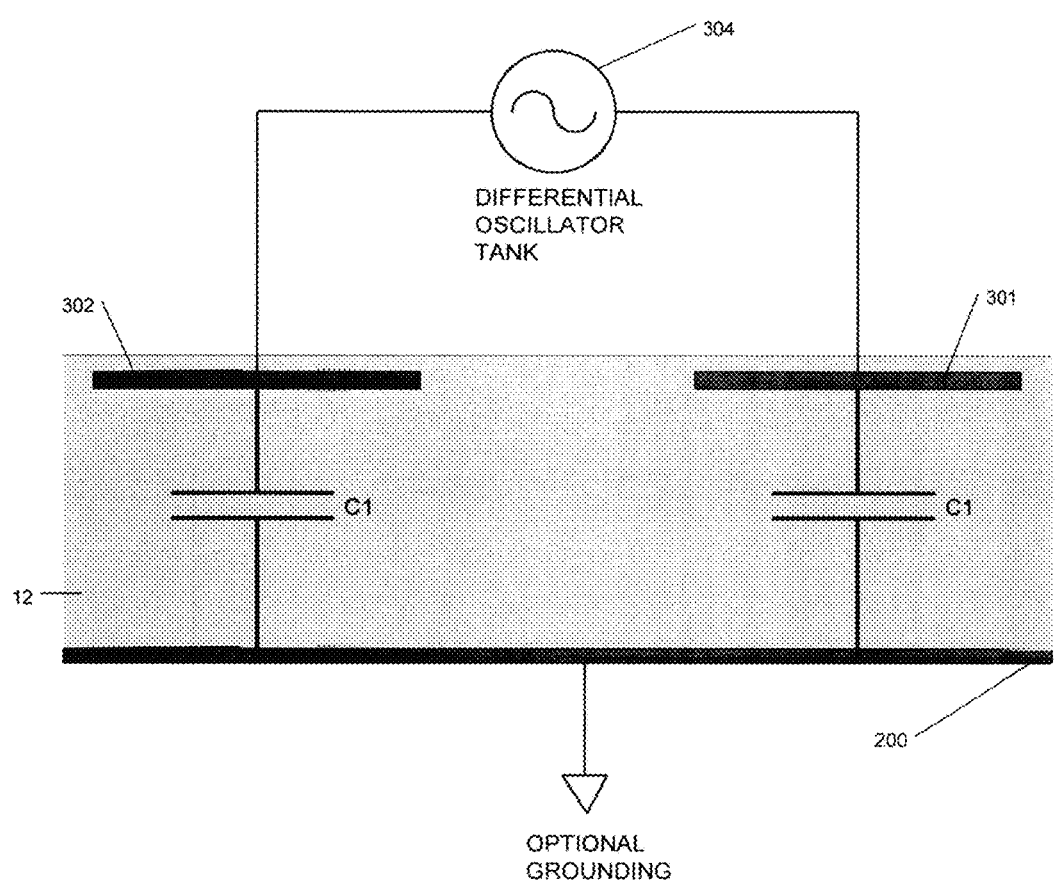
FIG. 26 is a cross-sectional view showing the dielectric stack up of electrodes in the cap while it is not screwed onto the bottle. Also shown is an oscillator using a differential resonant L-C (inductor-capacitor) tank with the tank capacitance determined by the electrodes in the cap.

FIG. 26 is a cross-sectional view showing the dielectric stack up of the electrodes in the cap 12 while it is not screwed onto the bottle 10. Also shown is an oscillator using a differential resonant L-C tank with the tank capacitance determined by the electrodes in the cap 12.

Figure 27:
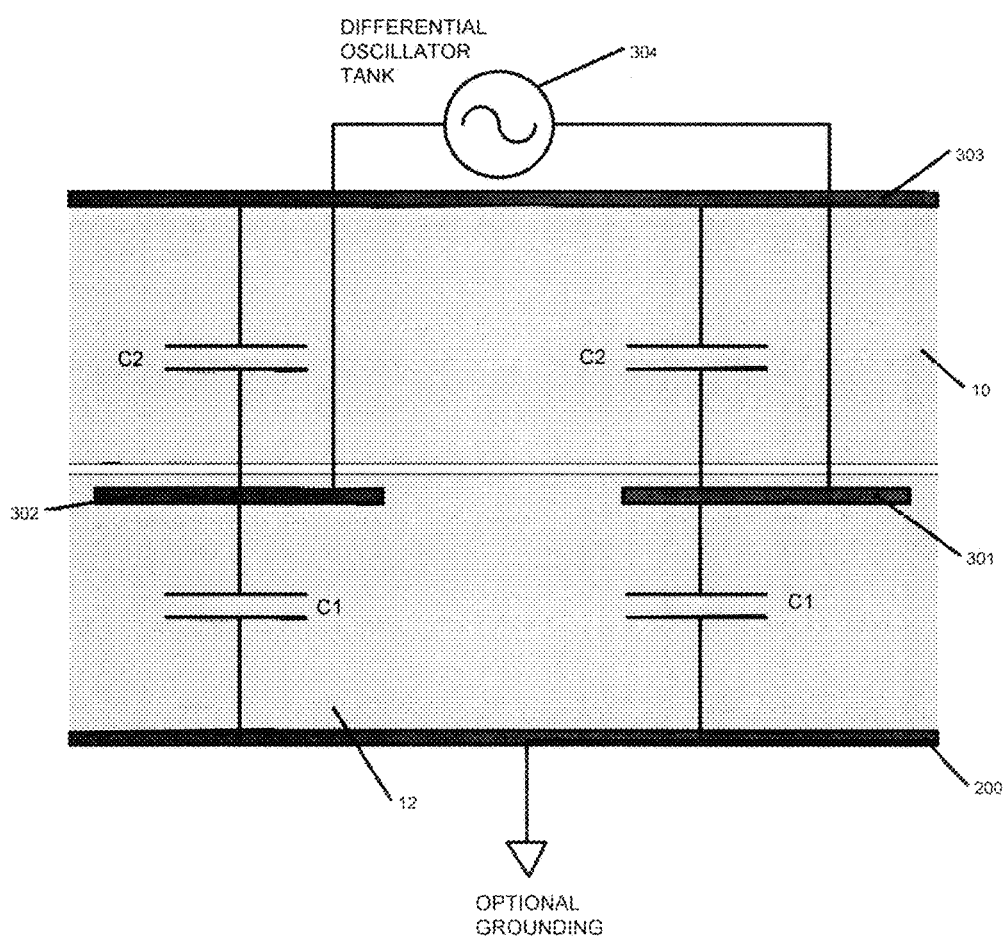
FIG. 27 is a cross-sectional view showing the dielectric stack up of electrodes in the cap while it is screwed onto the bottle. Also shown is an oscillator using a differential resonant L-C (inductor-capacitor) tank with the tank capacitance determined by the electrodes in the cap.

FIG. 27 is a cross-sectional view showing the dielectric stack up of the electrodes in the cap 12 while it is screwed onto the bottle 10. Also shown is an oscillator using a differential resonant L-C tank with the tank capacitance determined by the electrodes in the cap 12.

Figure 28:
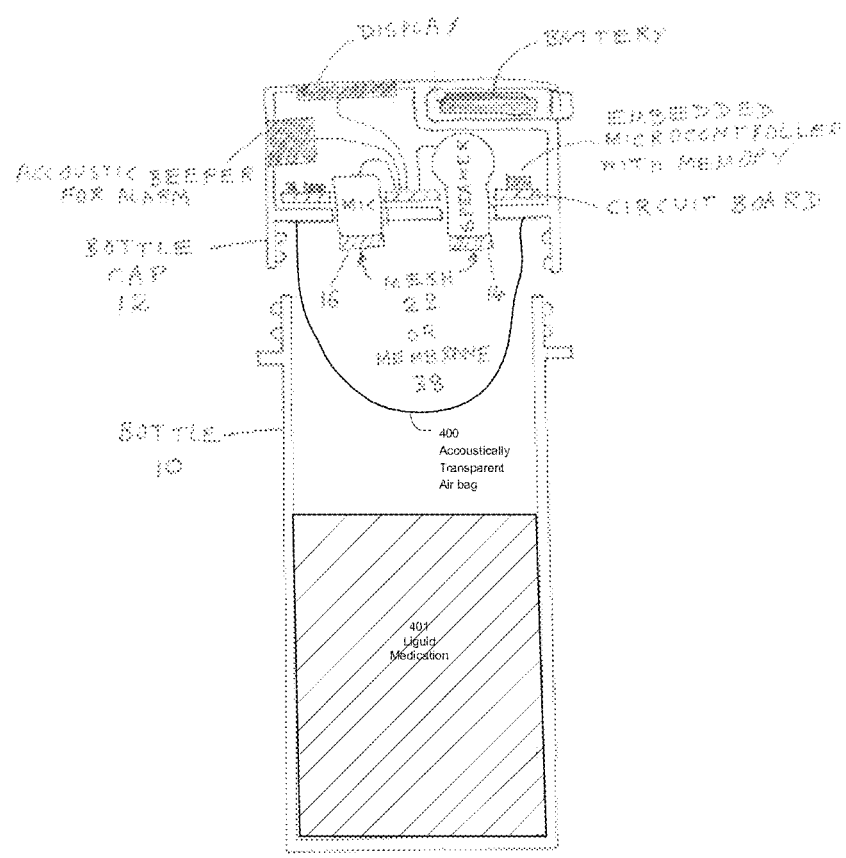
FIG. 28 is a cross-section of the bottle showing an exemplary placement of the microphone and speaker along with the associated electronics in the bottle cap, along with a protective air bag, for liquid medication.

FIG. 28 is a cross-section of the bottle showing an exemplary placement of the microphone and speaker along with the associated electronics in the bottle cap, along with a protective air bag, for liquid medication.

According to this invention, sound energy is used to determine if the medicine Bottle 10 containing Pills 20 or liquid medication is open or closed. The sound transducers comprising of a micro Speaker 14 and microphone 16, and the Electronics 18 including displays and audiovisual warnings, are housed in the cap 12 of Bottle 10 as shown in FIG. 1. They could optionally be housed at the bottom of the Bottle 10 or at the side of said bottle. A broadband OFDM Signal 24 is transmitted by the Speaker 14 periodically. When the Bottle 10 is closed, standing waves are produced inside the Bottle 10 enclosure, creating resonances at certain frequencies that are related to the length of the Bottle 10 enclosure. When the Bottle 10 is open, standing waves are not produced and there are no resonances, in the case where the Cap 12 houses the audio transducers. In the case where the Bottle 10 houses the audio transducers, standing waves are produced with resonances at frequencies that are different for each of the opened and closed conditions of said bottle. The measured resonance frequencies or the lack of it, are determined by taking the Fast Fourier Transform (FFT) of the received OFDM Signal 24 whereby measured frequency response information is obtained. By comparing said measured resonance frequencies or said measured frequency response information with those corresponding to a priori known and stored opened and closed state frequency responses, using spectral analysis algorithm 28, it can be determined if the Bottle 10 is opened or closed. When the Bottle 10 is open, there are no resonance frequencies for the case shown in FIG. 1 where the audio transducers are mounted in the bottle cap or on top of it. For the case where the audio transducers are mounted in the bottle or attached to it, the resonance frequencies are different for the opened and closed conditions of the bottle. The comparison of the measured and stored spectral information is done by taking a cross-correlation, followed by a windowed analysis of the peaks of the cross-correlation that results in the sum of the strong peaks around the largest peak, in the frequency domain. These values are known a priori for the open and closed conditions of the Bottle 10. If the sum is closer to the closed condition value of Bottle 10, then it is determined that the Bottle 10 is closed, otherwise it is determined that the Bottle 10 is open. Instead of using a combination of FFT and spectral analysis algorithm 28, one could use a time domain correlation method according to which the captured time domain signal waveforms are correlated with stored time domain waveforms that correspond to the open and closed conditions of the bottle 10. Based on the correlation results a decision could be taken to determine if the bottle 10 is opened or closed.

The resonance frequencies at various harmonics inside the Bottle 10 due to standing waves are related to the length of the resonating chamber as shown in FIG. 2. The relationship between the harmonic frequencies 'f' in the length 'L' of the enclosure is shown in FIG. 3. By using the un-modulated OFDM Signal 24 for channel sounding, all these harmonic frequencies can be determined by taking the FFT of the received signal followed by further post-processing to determine the peaks in the frequency domain where these resonances occur. By un-modulated OFDM it is meant that the amplitude and phase of each subcarrier of the OFDM signal is constant over time during which the samples for the FFT or analysis are taken. In case of liquid medication in an upright Bottle 10, the length L of the resonating chamber between the cap and the liquid surface is accurately computed from the harmonic frequencies f, and this determines the volume of liquid in the Bottle 10, thereby enabling the monitoring of the liquid medication consumption 40. In one embodiment of the patent, only the liquid level is monitored in a liquid medication dispensing system using said measurement of resonance frequencies.

For determining if the Bottle 10 is open or closed, it is not required to know the value of the resonance frequencies. All we need to know is how the spectrum of the received signal correlates with those of the stored spectra corresponding to the open condition and to the closed condition of the Bottle 10.

The microphone 16 and the Speaker 14 are protected by a fine Mesh 22 that keeps large particles of the medication from entering the devices. Fine powder that can go through the Mesh 22 does not affect the performance of these transducers. In case of liquid medication the Mesh 22 can be replaced with a thin acoustically transparent membrane 38. In one embodiment of the patent as shown in FIG. 28, the audio transducers are surrounded by an acoustically transparent air bag 400 that is used to physically isolate the audio transducers from the liquid medication 401. FIG. 28 shows the cross section of this embodiment. The air bag could be made of thin flexible polythene or suitable material. The microphone 16 could be a small electret microphone 16 or a small coil microphone 16. The Speaker 14 can use the same technology as found in earphones and ear buds that mostly use a moving coil with a stationary Neodymium permanent magnet. The enclosure of the Speaker 14 must be completely sealed to avoid back channel coupling to the microphone 16 from outside of the closed bottle. Sound from the Speaker 14 should only come out from the main opening and not from behind enclosure or from the sides, otherwise the resonances will not be detected with sufficient signal to noise ratio.

The signal processing components are shown in FIG. 5. The Speaker 14 is driven by a digital to analog converter (D/A), and the microphone 16 is sensed by an analog to digital converter (A/D). A microcontroller along with optional digital signal processor (DSP) and hardware accelerators, and together with program and data memory, timers and counters, and one or more clock sources, is used for the signal processing. An amplifier may optionally be included in the D/A to drive the speaker. An amplifier may optionally be included in the A/D to amplify the microphone signal. Low-frequency 32 kHz crystal oscillator can be used for the timekeeping. A high frequency clock with 0.1% stability can be used for the microcontroller and the sampling clock. An LCD display can indicate the time elapsed since the last medication. A buzzer or beeper can sound an alarm to indicate that it is time to take the medication.

The transmit OFDM waveform can either be stored in memory or computed each time, for example using an Inverse Fast Fourier Transform (IFFT) process using frequency domain stored information. Since it takes many seconds to open a Bottle 10 and take the medication, the channel sounding can be done every 4 to 5 seconds to determine if the Bottle 10 has been opened. Faster channel sounding can be performed at the expense of increased battery drain. Peak to average power ratio (PAPR) Reduction Code using complimentary code sequence is used for the channel sounding OFDM Signal 24 in order to achieve the maximum possible transmit signal level under the constraints of the limited battery supply voltage and D/A output power handling capability. This helps in increasing the output drive level by tens of dBs when large number of subcarrier tones are used, especially when better resolution of the resonance frequencies are required. For channel sounding, the OFDM Signal 24 is un-modulated, and a fixed sequence of the PAPR reducing complimentary code can be used. Generation of typical complimentary code sequence in Matlab® or FreeMat language is shown below in Table 1:

TABLE 1

```
% complementary code based phases
a0=[1]; b0=[1];
a1=horzcat(a0,b0); b1=horzcat(a0,-b0);
a2=horzcat(a1,b1); b2=horzcat(a1,-b1);
a3=horzcat(a2,b2); b3=horzcat(a2,-b2);
a4=horzcat(a3,b3); b4=horzcat(a3,-b3);
a5=horzcat(a4,b4); b5=horzcat(a4,-b4);
a6=horzcat(a5,b5); b6=horzcat(a5,-b5);
a7=horzcat(a6,b6); b7=horzcat(a6,-b6);
a8=horzcat(a7,b7); b8=horzcat(a7,-b7);
a9=horzcat(a8,b8); b9=horzcat(a8,-b8);
a10=horzcat(a9,b9); b10=horzcat(a9,-b9);
a11=horzcat(a10,b10); b11=horzcat(a10,-b10);
% Convert selected Complementary Code sequence to phase (0 or pi)
phasesSave=pi*(-a11'+1)/2;
phasesSave=phasesSave(1:NFFT); % select phase sequence for NFFT points
```

The array 'phasesSave' contains a sequence of phases each either zero or pi, and each phase is assigned as the phase of a corresponding subcarrier of the OFDM signal. The length of the array is NFFT which is the number of active tones used for channel sounding. Preferably NFFT is a power of two so that the PAPR is 3 dB for the envelope (or 2 to 3 dB higher for a real signal). In one embodiment of the patent, for the case when NFFT is not a power of two, then a search is made over a longer complimentary code sequence taking NFFT contiguous elements from the sequence to find the lowest PAPR. A typical Matlab® or FreeMat code performing this search is shown below in Table 2:

TABLE 2

```
R=64; % number of active tones
skip=1; % every "skip" tone is used, with skip-1 null tones inbetween
S=1; % frequency factor of 1st used tone above DC (set to > skip/2 so 1st used tone has fully symmetric spectrum)
FstepActiveTones=1000; % frequency spacing between active tones
Fstep=FstepActiveTones/skip; % FFT tone spacing in Hz, also fundamental tone
NFFT=2^nextpow2((S+R*skip+integer_offset)*2) % FFT size
Tfft=1/Fstep; % FFT period
Fs=Fstep*NFFT; % base sampling frequency
Tstep=1/Fs; % base sampling time step
t=0:Tstep:Tfft-Tstep; % time points array for an FFT period
Lt=length(t); % number of time points in FFT's period = NFFT
Vtones=zeros(R,Lt); % memory allocation for time domain signals (active_tones x time_points)
for ii=1:NFFT/2-R,
selectPhase=zeros(1,R);
selectPhase(1:R)=phasesSave(ii:ii+R-1);
%% Add complementary code based phases to zero-phase un-modulated OFDM
freqarray=(S:skip:S+(R-1)*skip)*Fstep;
for k=1:R,
Ftone=(S+(k-1)*skip)*Fstep;
Vtones(k,:)=sin(2*pi*Ftone*t+selectPhase(k));
end;
%% Transmit OFDM Signal 24    Vcol=sum(Vtones); % add all tone signals for composite OFDM transmit signal in time domain
rms=(sum(Vcol.^2)/length(Vcol))^0.5;
pk=max(abs(Vcol))
crest_dB=20*log10(pk/rms)
PAPR(ii)=crest_dB;
end;
%% Select min PAPR
[C,ii]=min(PAPR);
selectPhase(1:R)=phasesSave(ii:ii+R-1);
for k=1:R,
Ftone=(S+(k-1)*skip)*Fstep;
Vtones(k,:)=sin(2*pi*Ftone*t+selectPhase(k));
end;
```

Complimentary phase based phase encoding of OFDM Signal 24 has been used in wireless communications over a long time. Details and References can be found in the book "OFDM for wireless communications systems" by Ramjee Prasad. U.S. Pat. No. 5,862,182 shows how to use complimentary code based PAPR reduction for OFDM based wireless data communications. FIGS. 17 through 20 show the impact of using complimentary code based PAPR reduction for the case of 16 and 64 subcarriers. The PAPR reduces by 7.5 dB for 16 subcarriers, and by 12 dB for 64 subcarriers when complimentary code based phase encoding is used for the OFDM subcarriers.

The signal processing blocks are shown in FIG. 5. A stored OFDM waveform is sent as an example, every four seconds through the digital to analog converter to the loudspeaker that is housed in the bottle's Cap 12 (or optionally at the base of the Bottle 10). A spectrum of the transmitted signal is shown in FIG. 6. It occupies a frequency band from 200 Hz to 20 kHz and is flat in that region. The received signal time domain waveform is shown in FIG. 7. There is an initial transient settling due to the amplifier delay, and due to sound-wave propagation time that results in the buildup over time of the steady-state audio standing wave ratio in the Bottle 10 enclosure as measured by microphone 16 output signal voltage over time. In a particular implementation, the frequency from 0 to 44.1 kHz is divided into 1024 subcarriers. Subcarriers with frequencies below 200 Hz or above 20 kHz are forced to 0 amplitude. The FFT duration which is equal to 1 OFDM symbol duration Tfft is approximately 23 ms. Cyclic prefix or postfix is not used in the OFDM symbol since standing wave has to be measured in steady-state. Multiple identical OFDM symbols are consecutively transmitted without any idle time gaps between them. The receiving microphone 16 is digitized using the analog to digital converter and then optionally filtered in the time domain, after which the FFT is taken over multiple OFDM symbols. The FFT for each OFDM symbol can be averaged over multiple symbols, or the FFT of many OFDM symbols can be taken together and the resultant frequency domain output of the FFT can be decimated to get back to the original FFT size per symbol. This averaging process helps in mitigating interference. The FFT output is shown in FIG. 8 for closed and open Bottle 10 conditions. There are strong spikes at the harmonic frequencies for the closed Bottle 10. The spectrum is rather flat for the open condition and it basically shows the frequency response of the combined Speaker 14 and microphone 16 placed next to each other in the Cap 12 of Bottle 10. FIG. 9 shows the frequency response of the closed Bottle 10 when normalized to the frequency response of the open condition that is taken as the reference response. FIG. 10 shows the spectral correlation between a closed Bottle 10 condition and an earlier restored closed Bottle 10 spectrum. FIG. 11 shows the correlation of the closed Bottle 10 spectrum with an earlier stored open Bottle 10 spectrum. Since the Bottle 10 is closed, FIG. 10 shows a much stronger correlation peak. FIGS. 12 and 13 correspond to FIGS. 10 and 11 but with only the peaks of the correlation retained through a windowed analysis. If the sum of the waveform in FIG. 12 is greater than that in FIG. 13 then the Bottle 10 is assumed to be closed as is the case in these figures. The normalized frequency response of the open Bottle 10 condition is shown in FIG. 14 and ideally it should be perfectly flat. FIG. 15 shows the correlation of the open Bottle 10 spectrum with that of an earlier stored open Bottle 10 spectrum. The windowed analysis for this is shown in FIG. 16. For the open Bottle 10 condition the sum of the waveform in FIG. 16 is compared to the sum of the waveform in FIG. 13. As shown in FIG. 5, a long-term averaged spectrum of closed bottle 30 is computed and used to update the reference spectrum corresponding to the closed Bottle 10. The open Bottle 10 reference spectrum need not be updated as it is independent of the contents of the Bottle 10. The closed Bottle 10 reference spectrum can be preloaded at the factory based on a typical response.

A display and alarm program as shown in FIG. 5 checks the open and closed condition of the Bottle 10. If the Bottle 10 has not been opened for more than a predetermined time after it was last opened, then an alarm is sounded using a buzzer or beeper. Higher levels of warring can be given for example with more frequent beeping repeating every half an hour in case the medication is not taken beyond a certain time-lapse deadline.

In an embodiment of the patent, when the medicine Bottle 10 rolls out of the factory, the microcontroller is activated and it starts monitoring the opening of the Bottle 10. A green LED blinking light could indicate that the Bottle 10 has not been opened or an alphanumeric display could indicate the same. When the Bottle 10 is opened for the first time the LED color could be changed, or the read-out of the LCD display could show that the Bottle 10 has been opened, thereby indicating that either the Bottle 10 has been tampered or is being used by the customer. The firmware ensures that the LED will never show green color again or that the LCD display would not show that the Bottle 10 has not been opened earlier, once the opened state of the bottle is detected. If the Bottle 10 has a replaceable battery, then the Bottle 10 opened condition status should be permanently recorded in Flash memory, so that even after a subsequent power-on with the replaced battery, the Bottle 10 cannot be passed as a new un-opened product. The acoustic spectral correlation method ensures a foolproof tamper detection mechanism 34 as it is very difficult or if not impossible to defeat the audio signal processing. As an additional embodiment, if the product sits on the retail shelf for too long beyond its expiry date and the battery level starts dropping, the firmware monitors the battery level and writes into the Flash if it drops below a certain voltage. There is also a sufficiently large bypass capacitor that would allow sufficient time for the microcontroller to execute this part of the code even if the battery were to be removed. Upon next power on a tamper would be indicated if the voltage had dropped below the given threshold as indicated by an entry in the flash memory.

An optional wireless transmission device as shown in FIG. 5 connects that product to a medication compliance monitoring 36 and administration service. A local wireless LAN access point or a dedicated base station using proprietary or established wireless standards could be used as a bridge between the medicine Bottle 10 and the medication compliance monitoring and administration network. An optional USB port could be used in the Bottle 10 for periodically connecting to a computer and eventually through that to the medication compliance monitoring and administration network. Through the wireless device or the USB connection the user could download and analyze the medication history for the medicine Bottle 10, and a refill could be ordered automatically when the medication left in the Bottle 10 is nearing an end. An optional RFID device can be included in the electronics 18 as part of the wireless device for communicating with the point-of-sale terminal or with a close-proximity network-enabled sensing device at the user's premises for connecting to the medication compliance monitoring system. The wireless transmission device as shown in FIG. 5 could be a transmit-only device periodically sending data, or it could also have a wireless receiver, and could comply to a wireless standard like IEEE802.11n, or communicate through a proprietary protocol and physical layer.

The medical reminder device needs to serve bottles of different sizes and shapes. For each bottle 10 type the associated open and closed condition broadband spectral response is preloaded into the firmware at the factory especially if it needs to function as tamper detection device. Otherwise, if only the medication reminder functionality is needed, then these frequency responses could be collected on the fly when the unit is powered up or down by the user. The device could also be made available for retrofit application so that it could be mounted onto any desired bottle 10 cap 12. As an example, a hole could be punched into an existing bottle cap for allowing the microphone and speaker to have access to the bottle chamber. The retrofit device could be stuck to the top of the cap on the outside using glue or double-sided adhesive tape that is cut out to the shape of the retro fit unit along with the hole cut-out.

An example prototype Matlab® or FreeMat code that is intended to run in the firmware (after suitably translating to C-code and porting to the appropriate embedded microcontroller) for detecting the open and closed states of the bottle is shown below in table 3:

TABLE 3

```
ampl=10;
rept=34; % put 2^N+2
SampleRate = 44100; Tstep=1/SampleRate;
NFFT=1024; Fstep=SampleRate/NFFT; Tfft=1/Fstep;
Fmin=1000;
Fmax=20000;
% Fmin=0;
% Fmax=SampleRate;
Aftx=linspace(0,SampleRate-Fstep,NFFT); % put V(f)=f initially
Aftx(Aftx<Fmin)=0; Aftx(Aftx>Fmax)=0;
Amid=find(Aftx>0); Aftx(Amid)=-1i; % put V(Fmin<f<Fmax)=1i in frequency domain for sine wave generation in time domain
% complementary code based phases
a0=[1]; b0=[1];
a1=horzcat(a0,b0); b1=horzcat(a0,-b0);
a2=horzcat(a1,b1); b2=horzcat(a1,-b1);
a3=horzcat(a2,b2); b3=horzcat(a2,-b2);
a4=horzcat(a3,b3); b4=horzcat(a3,-b3);
a5=horzcat(a4,b4); b5=horzcat(a4,-b4);
a6=horzcat(a5,b5); b6=horzcat(a5,-b5);
a7=horzcat(a6,b6); b7=horzcat(a6,-b6);
a8=horzcat(a7,b7); b8=horzcat(a7,-b7);
a9=horzcat(a8,b8); b9=horzcat(a8,-b8);
a10=horzcat(a9,b9); b10=horzcat(a9,-b9);
a11=horzcat(a10,b10); b11=horzcat(a10,-b10);
phasesSave=pi*(-a11'+1)/2;
phasesSave=phasesSave(1:NFFT);
Aftx=Aftx.*exp(phasesSave'*1i); % modify phase based on CC to reduce PAPR
Aftx=Aftx.*exp(rand(1,NFFT)*2*pi*1i); % randomize phase to reduce PAPR
Ftx=0:Fstep:(SampleRate-Fstep);
figure(1); plot(Ftx(1:NFFT/2),abs(Aftx(1:NFFT/2))); title('Transmit Spectrum');
% convert to time domain sine-wave signal, for 1 FFT period
Aftx_rev=fliplr(Aftx);
Aftx1=[Aftx(1:NFFT/2) conj(Aftx_rev(NFFT/2:NFFT-1))]; % preprocess to produce sine wave tones
Attx=ifft(Aftx1); % signal is real due to above preprocessing
rms=(sum(Attx*Attx')/length(Attx))^0.5
display(['Mean Tx:']);display([mean(Attx)]);display(['Max Tx:']);display([max(abs(Attx))]); % ensure it is DC-free
PAPR=20*log10(max(abs(Attx))/rms)
Ttx=linspace(0,(Tfft-Tstep),NFFT);
figure(2); plot(Ttx,Attx); title('Transmit waveform for one FFT period');
Attx_long=repmat(Attx,1,rept);
% for ii=1:rept-1
%     Attx_long=[Attx_long Attx];
% end;
Ttx_long=linspace(0,(Tfft-Tstep),NFFT*rept);
figure(3); plot(Ttx_long,Attx_long); title('Transmit Waveform');
Attx_check=Attx_long(NFFT/2:1.5*NFFT-1);
Aftx_check=fft(Attx_check);
%figure(4); plot(Ftx,abs(Aftx_check)); title('check spectrum of actual transmit signal');
%figure(5); plot(angle(Aftx_check)); title('check spectrum of actual transmit signal');
nfilter = 10; Rp = 0.5;
Wn = [1000 20000]/(SampleRate/2);
[b,a] = cheby1(nfilter,Rp,Wn);
%figure(6); [y,t] = impz(b,a,101); stem(t,y); title('receiver filter impulse response');
% Vref_rx=zeros(1,NFFT*16);
reply='1';
%t = timer('StartDelay',NFFT*0.5*Tstep,'TimerFcn','disp("Hello World!")','Period', 2*Tfft);
while ~(reply=='d'),
%%Open the analog output device and channels
AO = analogoutput('winsound',0);
chan = addchannel(AO,1);
%% Set the sample rate and how long we will send data for
%% 44,100 Hz, 1 seconds of data
duration = rept*Tfft;
set(AO,'SampleRate',SampleRate)
set(AO,'TriggerType','Manual')
NumSamples = SampleRate*duration;
%% Create a signal that we would like to send, 500 Hz sin wave
data = ampl*Attx_long';
%% Put the data in the buffer, start the device, and trigger
putdata(AO,data);
%%Open the analog input device and channels
AI = analoginput('winsound',0);
chan = addchannel(AI,1);
duration2 = Tfft*rept;
SampleRate2 = SampleRate;
set(AI,'SampleRate',SampleRate2);
set(AI,'SamplesPerTrigger',duration2*SampleRate2);
```

TABLE 3-continued

```
set(AI,'TriggerType','Manual');
start(AO)
start(AI);
trigger(AO);
%start(t)
%wait(t)
trigger(AI)
data2 = (getdata(AI))';
%     figure(7); plot((1:duration2*SampleRate2)*Tstep,data2); title('Raw received signal');
data2_filter=filter(b,a,data2);
figure(7); plot((1:duration2*SampleRate2)*Tstep,data2_filter); title('Received Signal');
Vfrx=fft(data2_filter(NFFT*1.5:NFFT*(rept-0.5)-1)); % ??? ifft was used earlier
figure(20);subplot(2,1,1);plot(data2_filter);subplot(2,1,2);plot(abs(Vfrx));
%% compute fundamental spectrum (remove freq domain null tones)
Vfrx_base=Vfrx(1:(rept-2):length(Vfrx));
% %% compute alternate spectrum taking average of FFTs (should give same result)
%     Vfrx_avg=zeros(1,NFFT);
%     for ii=1:rept-2,
%         Vfrx_avg=Vfrx_avg+ifft(data2_filter( (NFFT*1.5+(ii-1)*NFFT :
NFFT*1.5+ii*NFFT-1)));
%     end;
%     Vfrx_avg=Vfrx_avg./(rept-2);
Frx=0:Fstep/(rept-2):(SampleRate-Fstep/(rept-2));
Frx_base=Frx(1:(rept-2):length(Frx));
%% save channel response reference spectrum in file
if reply=='2',
Vfrx_ref=abs(Vfrx_base);
fid1 = fopen('channel.bin','w');
fwrite(fid1,Vfrx_ref,'float32');
status = fclose(fid1);
end;
if reply=='5',
Vfrx_closed=abs(Vfrx_base);
fid1 = fopen('closed.bin','w');
fwrite(fid1,Vfrx_closed,'float32');
status = fclose(fid1);
end;
if reply=='7',
Vfrx_open=abs(Vfrx_base);
fid1 = fopen('open.bin','w');
fwrite(fid1,Vfrx_open,'float32');
status = fclose(fid1);
end;
%% Read channel, open and closed reference files
if reply=='1',
fid1 = fopen('channel.bin','r');
[Vfrx_ref,inf] = fread(fid1,'float32');
status = fclose(fid1);
Vfrx_ref=Vfrx_ref';
rms=(sum(Vfrx_ref.^2)^0.5)/(length(Vfrx_ref)^0.5) % note that Vfrx_ref is already saved as
absolute value.
ij=find(Vfrx_ref<rms/50);
Vfrx_ref(ij)=10*rms; % small channel responses are attenuated instead of being amplified
fid1 = fopen('open.bin','r');
[Vfrx_open,inf] = fread(fid1,'float32');
status = fclose(fid1);
Vfrx_open=Vfrx_open';
fid1 = fopen('closed.bin','r');
[Vfrx_closed,inf] = fread(fid1,'float32');
status = fclose(fid1);
Vfrx_closed=Vfrx_closed';
end;
Vfrx_nor=Vfrx_base./Vfrx_ref;
figure(8); plot(Frx_base,(abs(Vfrx_base)+0.001), Frx_base,(abs(Vfrx_ref))); xlabel('Frequency');
ylabel('Volts'); title('Received Spectrum and Channel Response'); grid on;
figure(9); plot(Frx_base, 20*log(abs(Vfrx_nor)+1e-6)); ylabel('dBV'); title('Channel normalized
spectrum');axis([0,SampleRate,-10,100]); set(gca,'XTick',0:SampleRate/10:SampleRate);
set(gca,'YTick',-10:10:100);
Vtrx=real(ifft(Vfrx)); % ??? fft used earlier
Trx=linspace(0,(Tfft*(rept-2)-Tstep),NFFT*(rept-2));
%     figure(10); plot(Trx,Vtrx); title('Received filtered time signal');
waittilstop(AI,2);
waittilstop(AO,2);
%% Find correlation with signatures
cor_val_closed = xcov(abs(Vfrx_base),abs(Vfrx_closed),NFFT,'coeff'); cor_val_open =
xcov(abs(Vfrx_base),abs(Vfrx_open),NFFT,'coeff');
figure(11); plot(cor_val_closed); title('Closed Bottle 10 correlation'); figure(12);
plot(cor_val_open); title('Open Bottle 10 correlation');
cratio=max(cor_val_closed)/max(cor_val_open);
%% Select only local correlation peaks over window of +-win
```

TABLE 3-continued

```
len=length(cor_val_closed);
c1(1:len)=0;
win=20;
win2=600;
for jj=win+1:len-win-1,
if (cor_val_closed(jj)>max(cor_val_closed(jj-win:jj-1))) &
(cor_val_closed(jj)>max(cor_val_closed(jj+1:jj+win))),
c1(jj)=cor_val_closed(jj);
end;
end;
cor_val_closed=c1;
cor_val_closed(1:win2)=0;cor_val_closed(len-win2:len)=0;
c1(1:len)=0;
for jj=win+1:len-win-1,
if (cor_val_open(jj)>max(cor_val_open(jj-win:jj-1))) &
(cor_val_open(jj)>max(cor_val_open(jj+1:jj+win))),
c1(jj)=cor_val_open(jj);
end;
end;
cor_val_open=c1;
cor_val_open(1:win2)=0;cor_val_open(len-win2:len)=0;
figure(13); plot(cor_val_closed); title('windowed Closed Bottle 10 correlation'); figure(14);
plot(cor_val_open); title('windowed Open Bottle 10 correlation');
%% select only a certain range (=divval) of correlations value below the peak
divval=10;
jj=find(cor_val_closed>max(cor_val_closed)/divval);
cor_closed=cor_val_closed(jj);
jj=find(cor_val_open>max(cor_val_open)/divval);
cor_open=cor_val_open(jj);
sum_open=sum(cor_open)/cratio; sum_closed=sum(cor_closed); display([sum_closed]);
display([sum_open]); display([cratio]);
if sum_closed>sum_open,
display('CLOSED');
else
display('OPEN');
end;
%% Moving average spectral filtering
% windowSize = 50;
% Vfrx_filter=filter(ones(1,windowSize)/windowSize,1,abs(Vfrx));
% figure(12); plot(Frx, abs(Vfrx_filter)); title('Moving averaged spectrum');
reply = input('1 or Enter=correlate, 2=save channel response, 5=save closed response, 7=save
open response, d or other keys=exit: ','s');
if isempty(reply)% | reply=='1',
reply='1';
else
if reply=='2'|| reply=='5' || reply=='7',
else
reply='d';
end;
end;
end;
%% clean up, close down
delete(AI);
clear AI;
delete(AO);
clear AO;
close all;
status=fclose('all');
```

In one embodiment of the patent, projected capacitance measurements are used to determine if the bottle 10 is opened or closed. FIG. 21 shows the electrodes in the side-wall of cap 12. The outer surface of the cap 12 has a conductive metallized plastic layer 200 to electrostatically shield the inner electrodes. The inner conductive electrodes are flush with the inner surface of the cap 12 side-wall that overlaps with the side-wall of the mouth of bottle 10. The inner conductive electrodes comprise of a larger drive electrode 201 and smaller sensor electrodes 202. The drive electrode 201 is sandwiched between the sensor electrodes 202 and the outer shield 200. All these three electrodes are separated from each other by a dielectric material that comprises the cap 12 material or some suitable dielectric material. FIG. 23 and FIG. 24 show the dielectric stack up for the cap 12 alone and for the cap 12 the bottle 10 when the cap 12 is screwed onto the bottle 10 respectively. FIG. 22 shows the signal processing involved with the projected capacitance measurement of the capacitance between the drive and the sensor electrodes. A sine wave oscillator 301 injects a tone onto the drive electrode. Due to the projected mutual capacitance Cm between the drive and sensor electrodes, the tone is picked up by the sensor electrodes and amplified by the amplifier 304. This signal is further filtered by lowpass or bandpass filter 305 after which it is digitized and down-converted to DC by the multiplier 307. The output of the multiplier 307 is integrated by 308 and then sampled by a sample and hold switch 309. The sampled value is compared to a known value C 311 and the comparator output Nout 312 is used to determine if the bottle 10 is opened or closed. This operation is repeated at regular intervals. The outer shield 200 protects the drive and sensor electrodes from electrostatic influences of external objects like the human hand and electrical wiring or electrical gadgets. FIG. 23 shows the electrostatic field lines when the cap 12 is not placed onto the bottle 10. In this case most of the electric field lines between the drive and sensor electrodes are limited to the space between the two electrodes. The capacitance between the drive and sensor electrodes is basically the bottom plate capacitance of the sensor electrode. When the cap 12 is screwed onto the bottle 10 as shown in figure at 24, the dielectric material of the bottle 10 appears on top of the sensor electrodes. Because the dielectric constant of the bottle 10 is significantly larger than that of air, more field lines from the drive electrode couple to the sense electrodes when the bottle 10 is present. This increases the mutual capacitance between the drive and sensor electrodes, and this change in mutual capacitance is used to determine whether or not the cap 12 has been screwed onto the bottle 10.

In another embodiment, the mouth of the bottle i.e. the end of the bottle 10 that overlaps with the cap 12, has an embedded conductive film 303 that influences the capacitance between two electrodes 301 and 302 that are placed in the cap 12. Such an arrangement is shown in FIG. 25 which is the top cross-sectional view of the cap 12 and bottle 10 together. The inner surface of the cap 12 has as an example two electrodes 301 and 302 and the capacitance between these two electrodes increases significantly when the conductive surface 303 of the bottle 10 overlaps with these electrodes when the bottle is closed. The outer surface of the cap 12 has a conductive electrode 200 to protect and isolate the inner two electrodes from electrostatic couplings arising from the human hand, electrical wiring and electrical gadgets. FIG. 26 shows the capacitance between the two inner electrodes when the bottle 10 is not present. The capacitance between the two electrodes is measured using an LC oscillator 304. This oscillator 304 has a differential tank circuit whose capacitance is largely due to the capacitance between the two electrodes. The frequency of this oscillator changes when the cap 12 is screwed onto the bottle 10 since the conductive surface of the bottle 10 increases the capacitive coupling between the two inner electrodes as shown in FIG. 27. The change in frequency of the oscillator is measured by the electronics 18 inside the cap 12, and it is used to determine if the bottle 10 is opened or closed. In one embodiment of the patent, the conductive film of the bottle 10 could be a conductive ring that could be slipped on to the inner surface of the bottle 10. The edge of the ring would have a flange that would be flush with the edge of the bottle 10 in order to ensure that the conductive ring stays fixed at the edge of the bottle 10. In one embodiment of the patent, if a liquid medicine significantly changes the capacitance between said electrodes, then a stopper material with low electrical dielectric constant $E_r$, can be plugged into the mouth of the bottle to keep the liquid away from the electrodes when the bottle is tilted or is upside-down.

In one embodiment of the patent, purchase details, dosage details, patient details, authenticity of the product and untampered status of the product at the retail pharmacy store can be electronically furnished to the patient monitoring and medication compliance and administration system network. The wireless or the USB device in the product is used to send this information through a local bridge or a wireless access point or computer onto the Internet or desired network.

Since other modifications and changes to fit particular operating requirements and environments will be apparent to those skilled in the art, the invention is not considered limited to the example chosen for purposes of disclosure, and covers all changes and modifications which do not constitute departures from the true spirit and scope of this invention. In particular it may be noted that the patent is applicable also to bottles, jars and containers that are not used for medicine, but are used for other items. For example, the patent is applicable to a jar containing bird seed, so that the bird owner can be reminded to open the jar to feed the birds. In particular it may additionally be noted that the patent embodiment using audio transducers is applicable also to containers holding liquid medicine for the purpose of measuring said liquid amount.

Having thus described the invention, what is desired to be protected by Letters Patent is presented in the subsequently appended claims.

What is claimed is:

1. A method of determining open and closed states of a medicine bottle for one or more purposes including a) reminding patients to take medication, b) detecting tampering of medicine bottle, and c) providing medicine usage inputs to a medication compliance monitoring and administrative system, the method comprising of:
    providing a medicine bottle which is able to hold medicine;
    providing a cap which can be opened, and which is able to retain medicine inside said medicine bottle;
    providing a plurality of conductive surfaces wherein said conductive surfaces are placed concentrically in the region between said medicine bottle and said cap when said bottle is closed with said cap, and wherein said conductive surfaces are electrically isolated from each other forming high electrical resistance between them;
    providing electronics which is able to measure capacitance between at least two of said conductive surfaces;
    providing means for mounting and housing said electronics;
    measuring capacitance between at least two of said conductive surfaces, and comparing said capacitance with a prior known capacitance value, and thereby determining therefrom whether said medicine bottle is opened or closed, using said electronics;
    wherein said cap includes providing a side wall with threading on inner surface that can be screwed onto the outer surface of the mouth of said bottle; and
    wherein said conductive surfaces includes a) providing an outer conductive shield on the outside surface of said cap, b) providing two separated conductive electrodes on the inner surface of said side-wall of said cap; and
    wherein said measuring of capacitance includes measuring capacitance between said two separated conductive electrodes on the inner surface of said side-wall of said cap.

2. The method of claim 1 wherein said conductive surfaces includes providing a conductive layer on the inner surface of the mouth of said bottle, whereby capacitance between said two separated conductive electrodes on the inner surface of said side-wall of said cap is significantly increased when said bottle is closed compared with when said bottle is open.

3. The method of claim 2 further comprising of:
    detecting tampering of a previously unopened and unused medicine bottle by periodically checking if said measured capacitance between at least two of said conductive surfaces deviates from a pre-determined closed bottle state capacitance value that is stored in memory during manufacturing or factory programming of said electronics.

4. The method of claim 1 further comprising of:
detecting tampering of a previously unopened and unused medicine bottle by periodically checking if said measured capacitance between at least two of said conductive surfaces deviates from a pre-determined closed bottle state capacitance value that is stored in memory during manufacturing or factory programming of said electronics.

\* \* \* \* \*